(12) United States Patent
Bergeron et al.

(10) Patent No.: US 7,947,064 B2
(45) Date of Patent: May 24, 2011

(54) STABILIZATION SYSTEM AND METHOD

(75) Inventors: Brian J. Bergeron, Austin, TX (US); K. Scott Ely, Cedar Park, TX (US); Charles R. Forton, Leander, TX (US); Jeremy J. Lemoine, Austin, TX (US); Peter T. Miller, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 739 days.

(21) Appl. No.: 11/946,644

(22) Filed: Nov. 28, 2007

(65) Prior Publication Data

US 2009/0138044 A1 May 28, 2009

(51) Int. Cl.
*A61B 17/70* (2006.01)

(52) U.S. Cl. .................... 606/263; 606/246; 606/103

(58) Field of Classification Search ............... 606/246, 606/264–279, 300–321, 103, 151
See application file for complete search history.

(56) References Cited

U.S. PATENT DOCUMENTS

| | | | |
|---|---|---|---|
| 5,658,286 A | 8/1997 | Sava | |
| 6,530,929 B1 | 3/2003 | Justis et al. | |
| 7,008,422 B2 | 3/2006 | Foley et al. | |
| 7,011,660 B2 | 3/2006 | Sherman et al. | |
| 7,083,621 B2 | 8/2006 | Shaolian et al. | |
| 7,087,058 B2 | 8/2006 | Cragg | |
| 7,137,985 B2 | 11/2006 | Jahng | |
| 7,188,626 B2 | 3/2007 | Foley et al. | |
| 7,250,052 B2 | 7/2007 | Landry et al. | |
| 7,563,274 B2 * | 7/2009 | Justis et al. | 606/279 |
| 2002/0082598 A1 | 6/2002 | Teitelbaum | |
| 2002/0147485 A1 | 10/2002 | Mamo et al. | |
| 2004/0215191 A1* | 10/2004 | Kitchen | 606/61 |
| 2005/0131407 A1 | 6/2005 | Sicvol et al. | |
| 2005/0251139 A1 | 11/2005 | Roh | |
| 2005/0277934 A1 | 12/2005 | Vardiman | |
| 2006/0265077 A1 | 11/2006 | Zwirkoski | |
| 2007/0055244 A1 | 3/2007 | Jackson | |
| 2007/0066977 A1 | 3/2007 | Assell et al. | |
| 2007/0162007 A1 | 7/2007 | Shoham | |

* cited by examiner

*Primary Examiner* — Eduardo C Robert
*Assistant Examiner* — Christina Negrelli
(74) *Attorney, Agent, or Firm* — Sprinkle IP Law Group

(57) ABSTRACT

The disclosure relates to systems and methods of spinal stabilization. Embodiments include methods of delivering a rod having a non-circular cross-sectional profile using a wire having an accommodating non-circular cross-sectional profile to inhibit movement of a rod relative to the wire. A surgical system can comprise a first sleeve advanced via a first incision to a vertebra, a second sleeve advanced via a second incision to another vertebra, a wire having a non-circular cross-sectional profile advanced via a third incision to the vertebrae and passed through the collars of bone fastener assemblies to extend from a fourth incision. A rod or a segment of a rod having a corresponding non-circular cross-sectional profile may be aligned with the wire and advanced and coupled with the vertebrae to stabilize the spine. After the rod is securely seated in the collars, the wire may be withdrawn from the body.

22 Claims, 30 Drawing Sheets

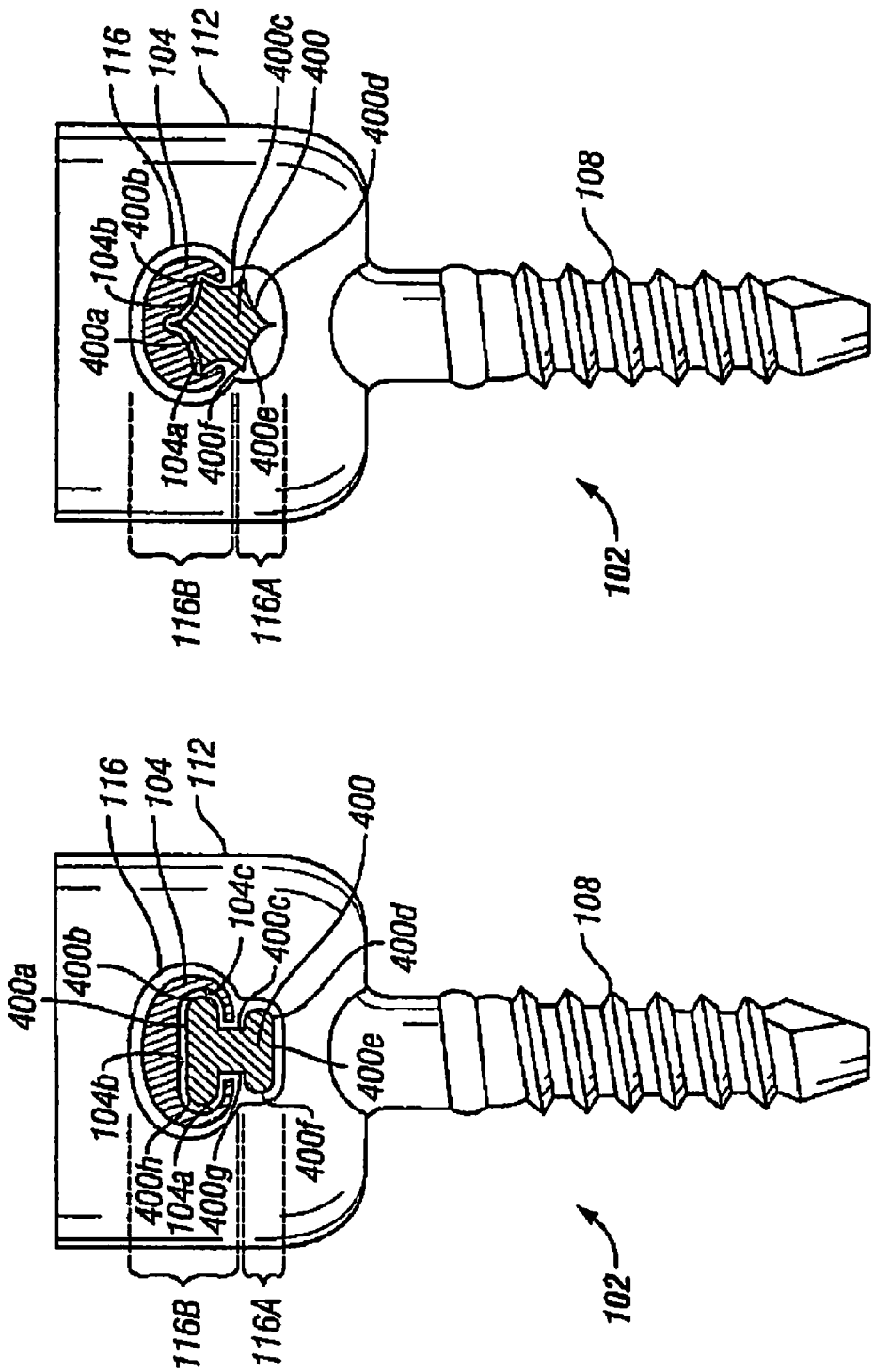

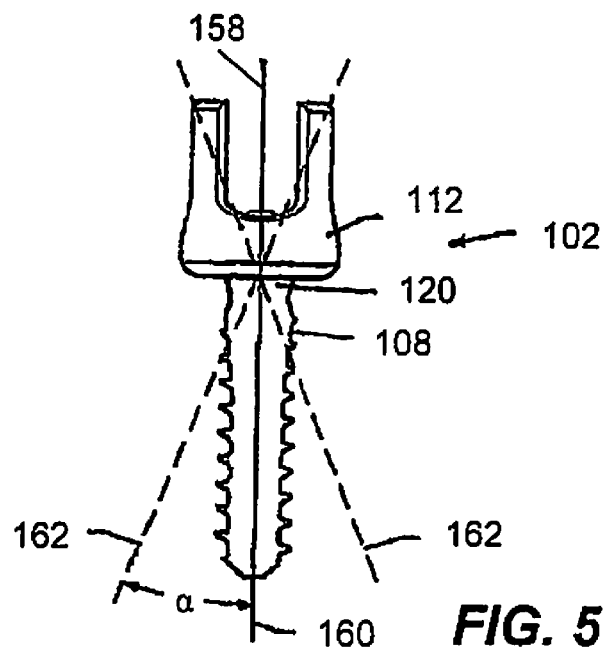
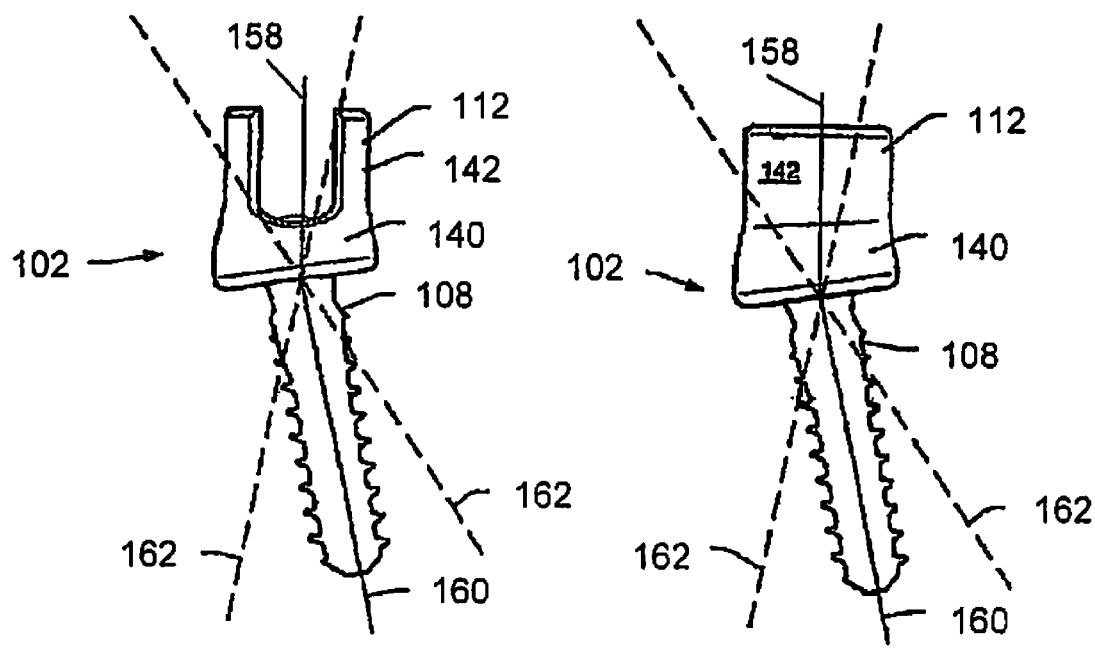
FIG. 5
FIG. 6A
FIG. 6B

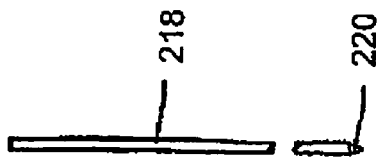
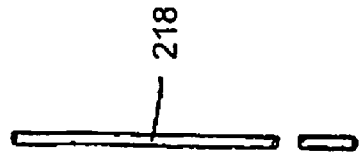
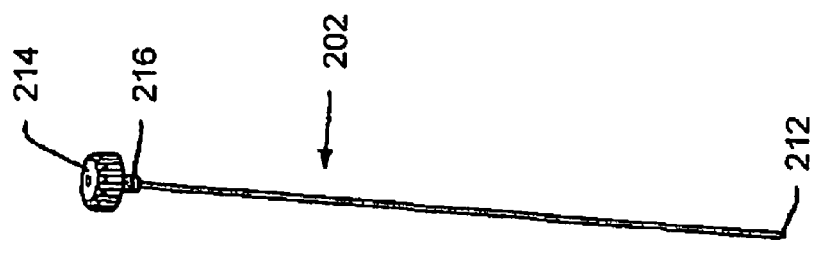
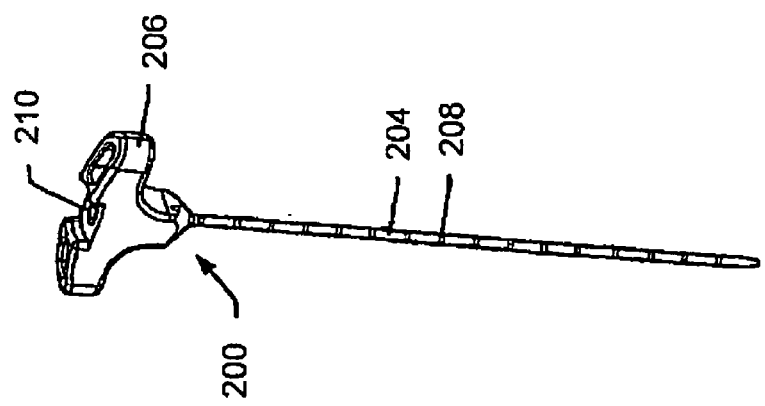
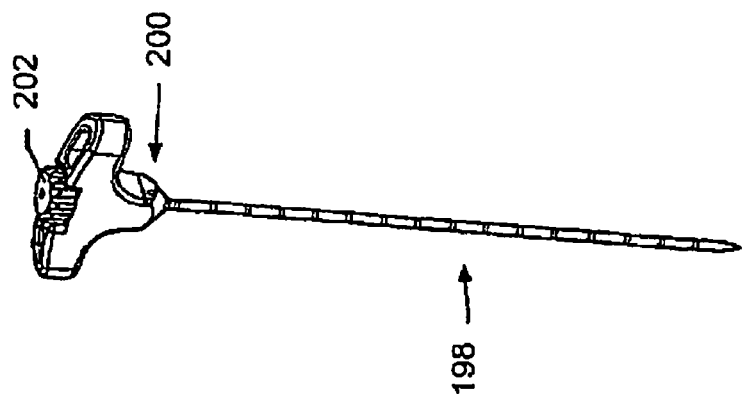

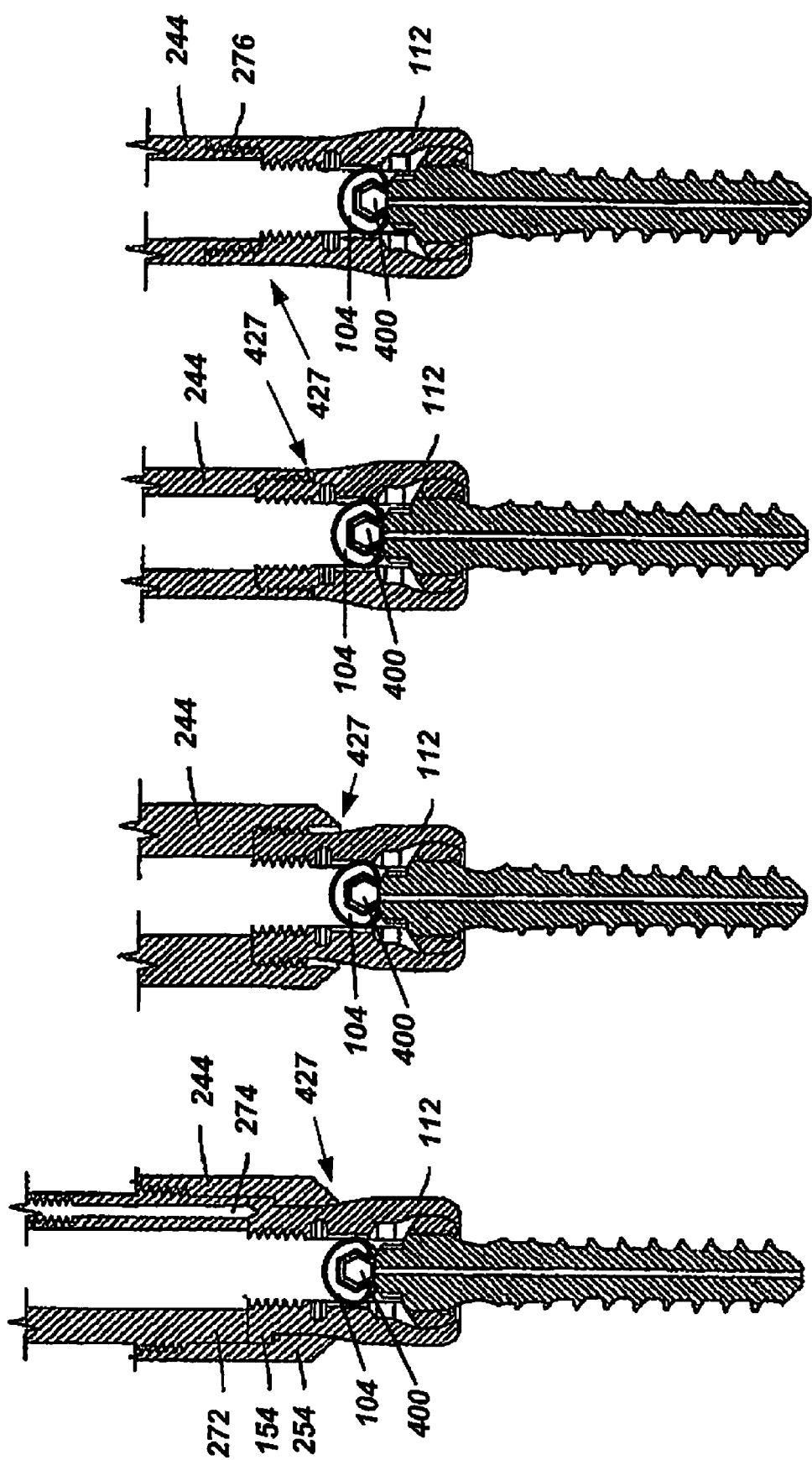

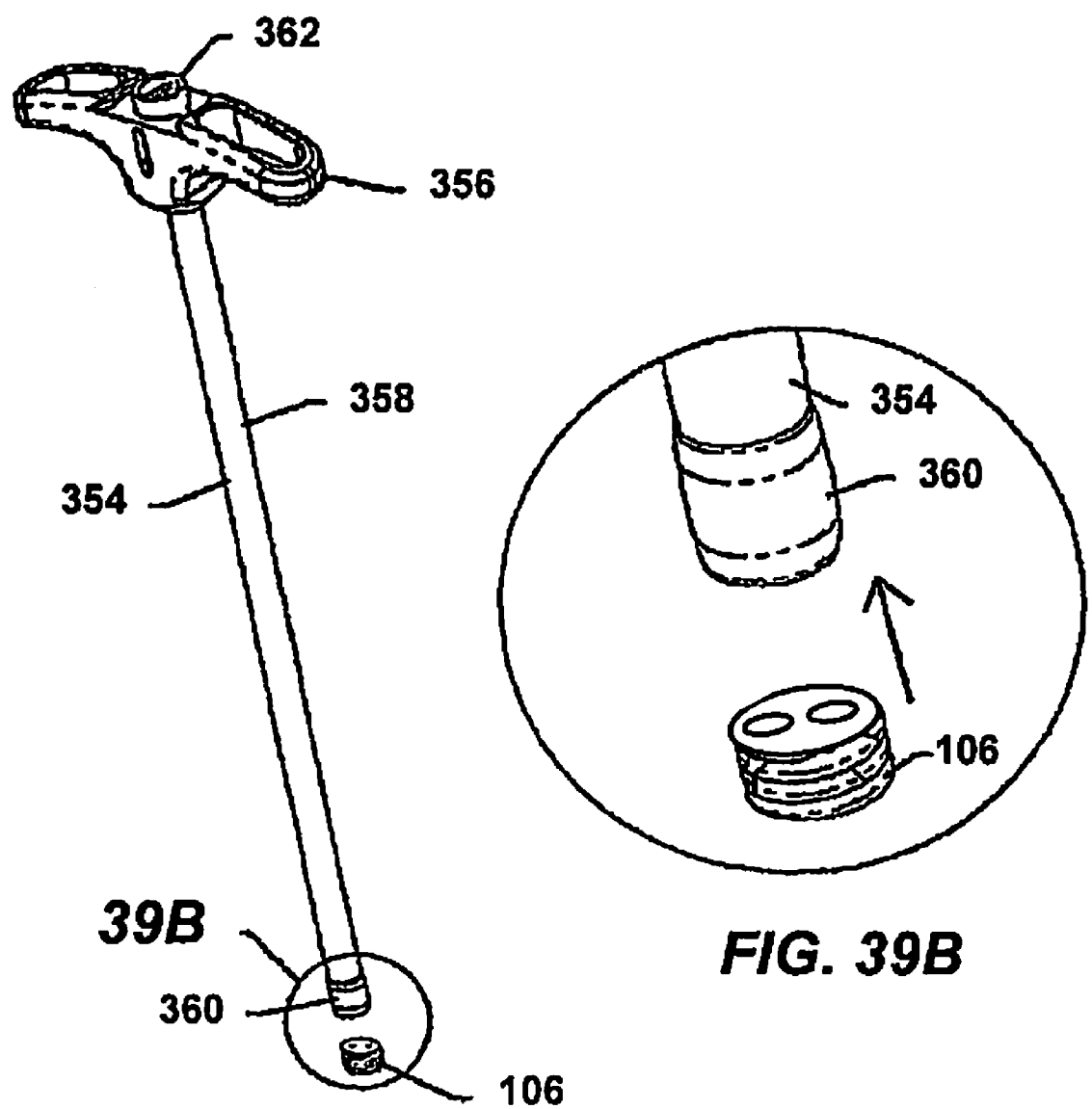

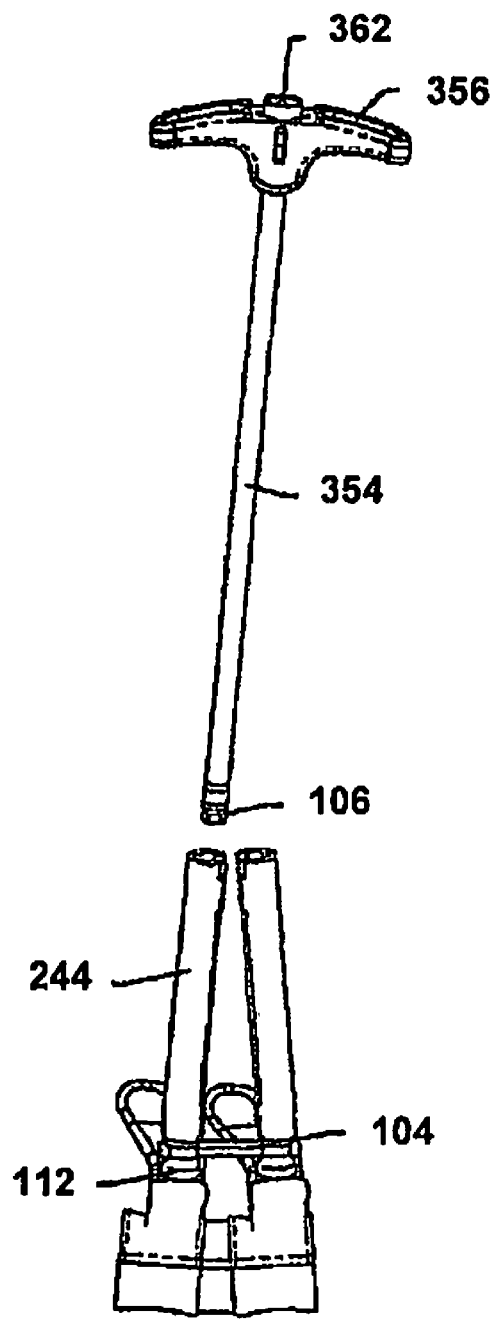 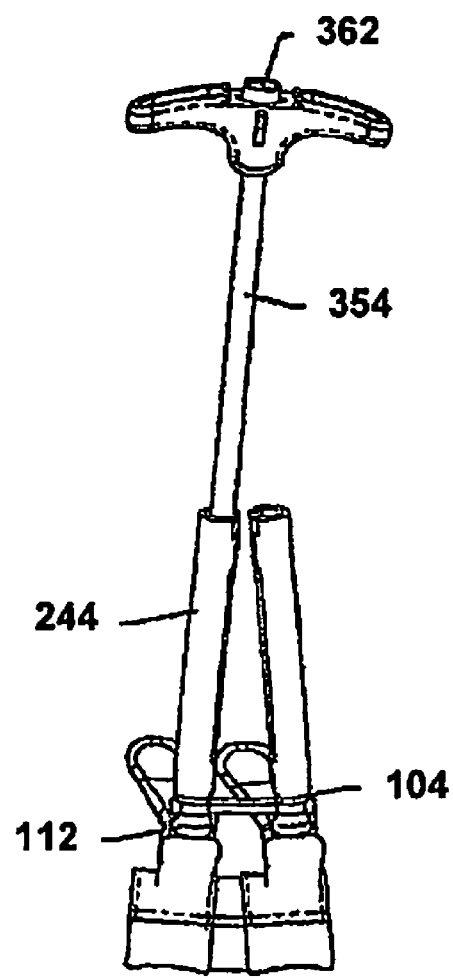
*FIG. 40A*  *FIG. 40B*

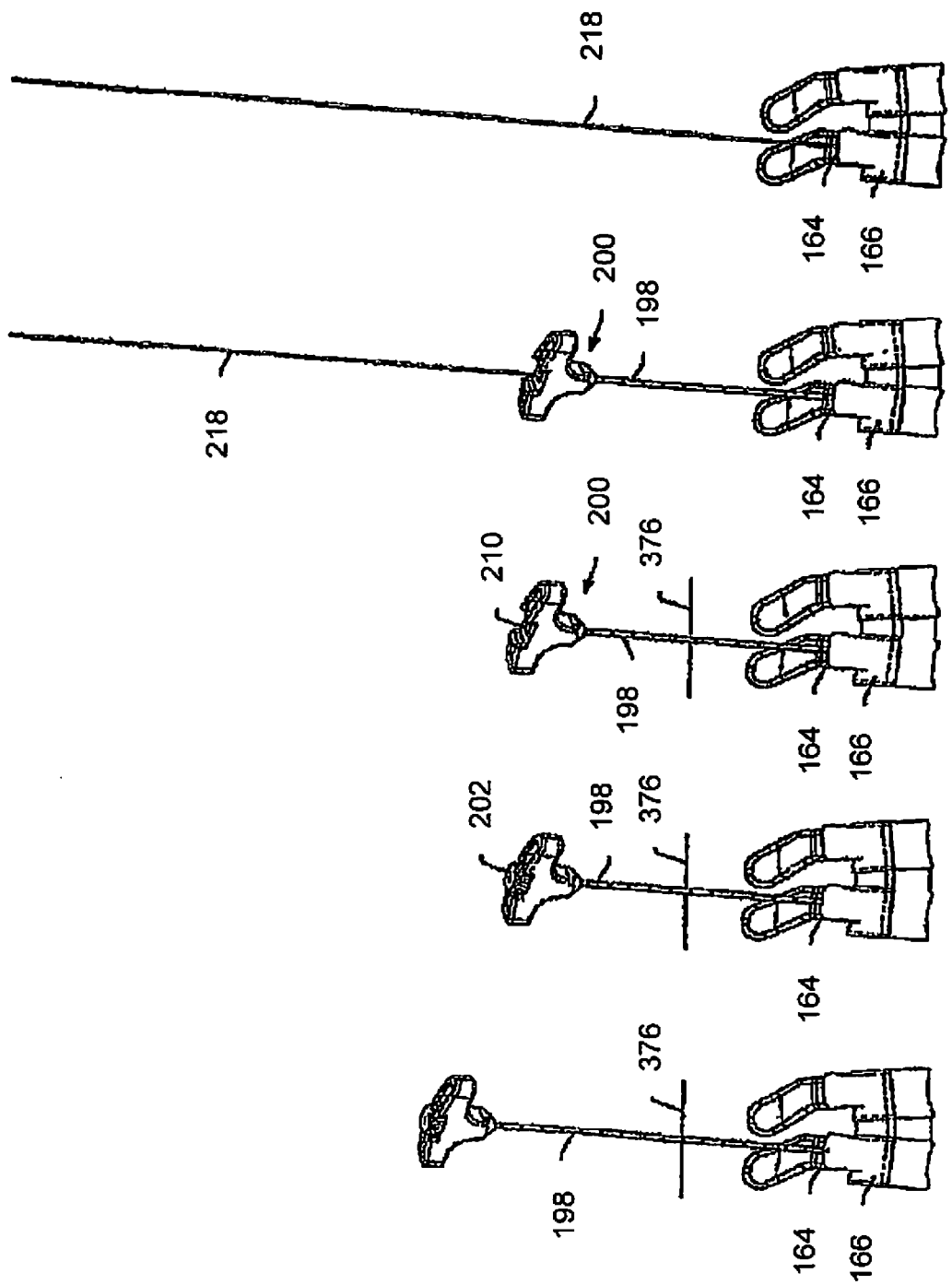

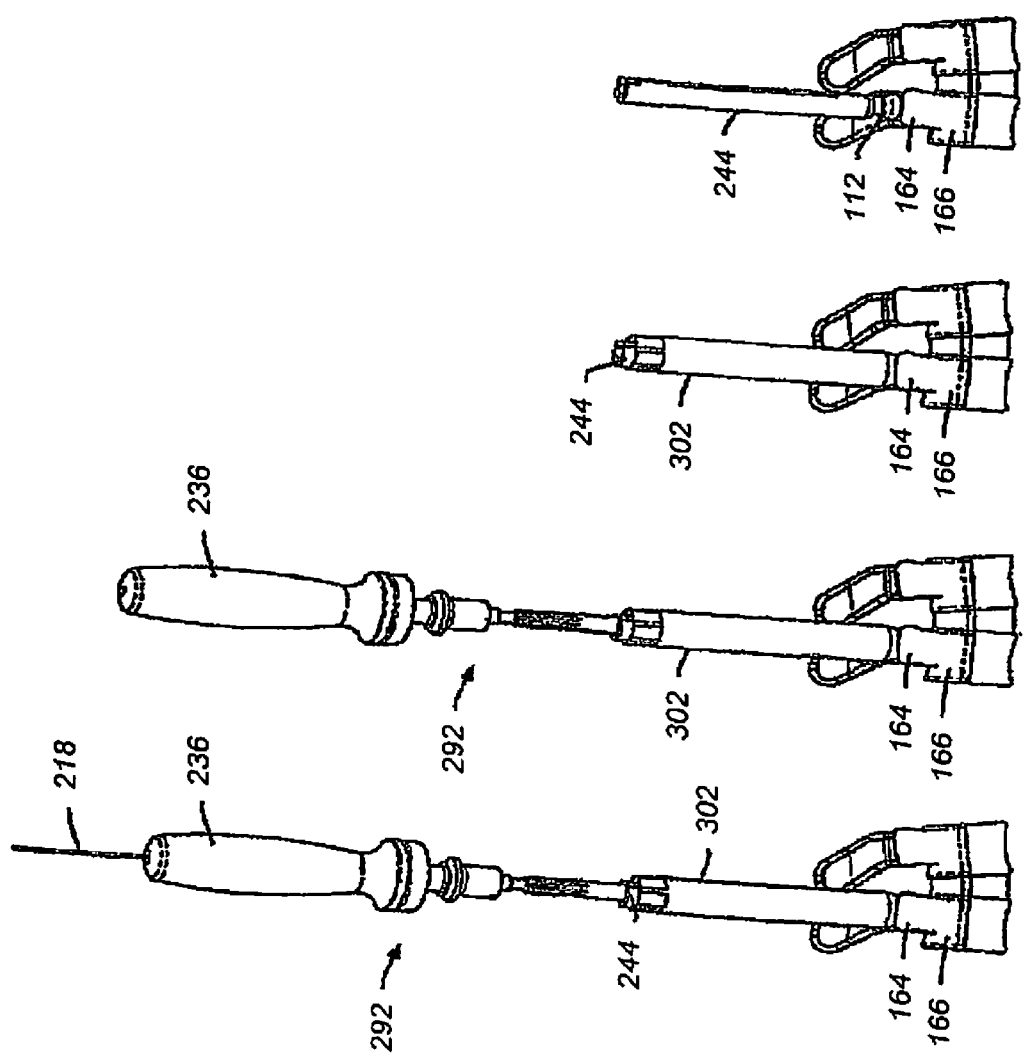

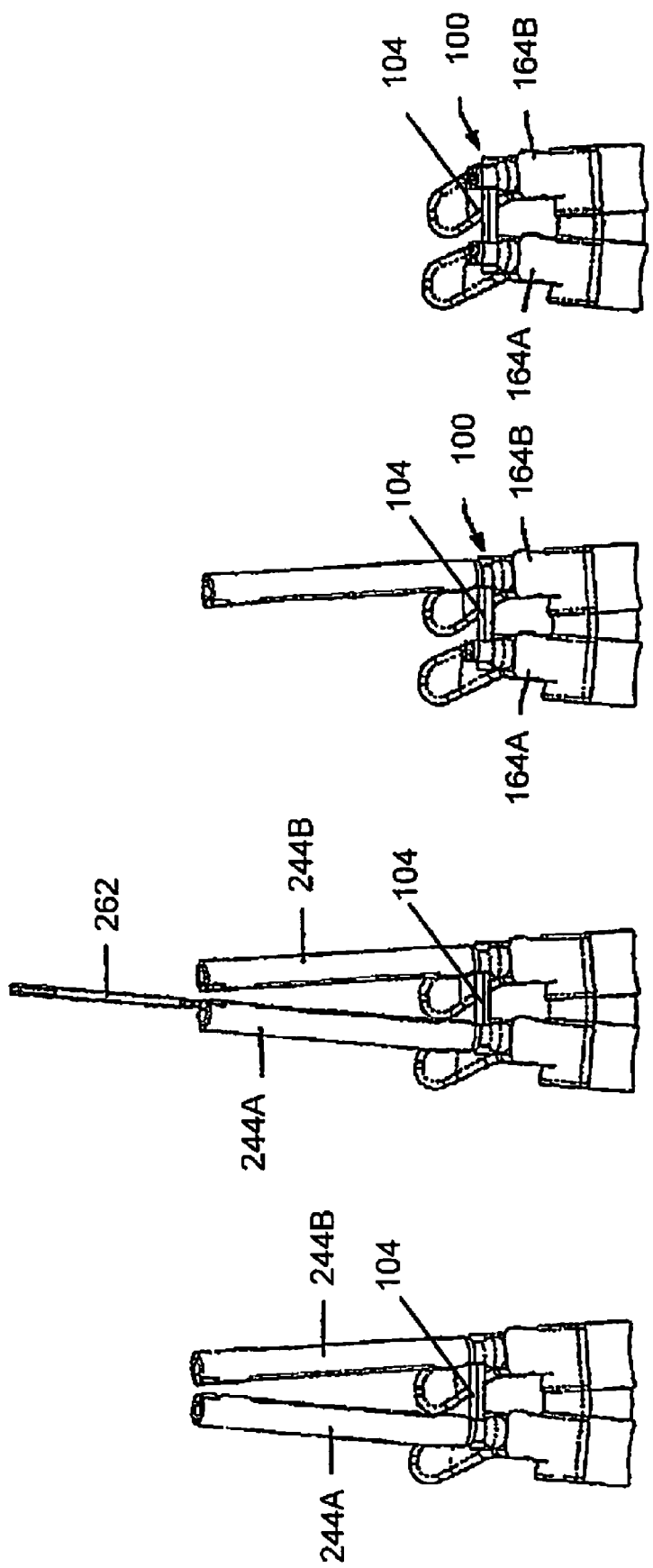

STABILIZATION SYSTEM AND METHOD

TECHNICAL FIELD OF THE DISCLOSURE

The disclosure describes various spine stabilization systems and methods, including systems and methods for inserting spinal stabilization rods in a minimally invasive surgery.

BACKGROUND OF THE DISCLOSURE

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spine stabilization procedure may be performed to maintain the natural spacing between vertebrae and promote spinal stability. Spinal stabilization may involve accessing a portion of the spine through soft tissue. Conventional stabilization systems may require a large incision and/or multiple incisions in the soft tissue to provide access to a portion of the spine to be stabilized. Conventional procedures may result in trauma to the soft tissue, for example, due to muscle stripping. Spine stabilization systems for a lumbar region of the spine may be inserted during a spine stabilization procedure using a posterior spinal approach. Conventional systems and methods for posterolateral spinal fusion may involve dissecting and retracting soft tissue proximate the surgical site. Dissection and retraction of soft tissue may cause trauma to the soft tissue, and extend recovery time.

SUMMARY OF THE DISCLOSURE

Minimally invasive procedures and systems may reduce recovery time as well as trauma to the soft tissue surrounding a stabilization site. The disclosure describes embodiments of systems and methods for spinal stabilization, particularly systems and methods that utilize a wire having a non-circular cross-sectional profile to deliver, preferably percutaneously, an elongated member (e.g., a rod). According to one embodiment, a system for stabilizing a portion of a spine comprises a rod having a non-circular cross-sectional profile and a length to span between two vertebrae, two bone fastener assemblies, and a wire for percutaneous advancement of the rod to the passage in a bone fastener assembly anchored to a vertebra. In some embodiments, the wire comprises a non-circular cross-sectional profile complementary to the non-circular cross-sectional profile of the rod for engaging the rod to inhibit rotational movement of the rod relative to the wire. In some embodiments, each bone fastener assembly includes a pedicle screw for advancement into a vertebra, a collar for coupling the rod to the pedicle screw, and a threaded closure member for engaging the threaded portion of the collar to couple the rod in a passage in the collar. A collar may have two upwardly extending walls forming a passage having a profile for receiving and accommodating a portion of the non-circular cross-sectional profile of the rod. A collar may have an opening forming a passage having a profile for receiving and accommodating a portion of the non-circular cross-sectional profile of the rod. In some embodiments, the non-circular cross-sectional profile of the rod may include an array of surfaces, a flange, a slot, a cannulated passage along a length of the rod, or a recessed portion along a length of the rod. In some embodiments, the rod comprises two segments, wherein each segment has a complementary non-circular cross-sectional profile for engaging the non-circular cross-sectional profile of the wire to inhibit rotational movement of the segment relative to the wire, a surface for engagement with a collar, a leading end for displacing tissue during advancement of a segment along the wire, and a trailing end comprising an engagement feature for connecting with an adjacent segment, wherein connecting the two segments forms a rod to span a vertebral level. In some embodiments, each segment comprises a cannulated passage through a portion thereof. In some embodiments, the cannulated passage extends along a central axis, is offset from a central axis, or is oriented askew to a longitudinal axis. In some embodiments, the rod comprises a curvature, bend, or angle along a length thereof. In some embodiments, the rod comprises a recessed portion located along the length and oriented transverse to the longitudinal axis. In some embodiments, the wire has a cross-sectional profile and a curvature for engaging the recessed portion. In some embodiments, the recessed portion is oriented at a selected angle relative to the longitudinal axis or a groove extending around at least a portion of the outer surface. In some embodiments, coupling a rod having a non-circular profile to a bone screw comprises positioning a portion of a wire having a non-circular cross-sectional profile complementary to the rod in a first passage through the collar and positioning a portion of the rod in the second passage and engaging a closure member in the collar. In some embodiments, engaging the closure member provides sufficient clearance for the wire to be withdrawn. In some embodiments, engaging the closure member securely couples the wire and rod to the bone screw.

According to another embodiment, a method for stabilizing a portion of a spine comprises the steps of making a first incision for anchoring a first bone fastener assembly in a first vertebra, making a second incision for anchoring a second bone fastener assembly in a second vertebra, making a third incision for entry of a wire having a non-circular cross sectional profile, making a fourth incision for exiting of the wire, advancing the wire through the third incision for positioning near the first and second bone fastener assemblies, engaging a rod with the wire, rotating the wire to rotate the rod, and securing the rod to the first and second bone screws, wherein the rod spans at least one vertebral level. In some embodiments, a bone fastener assembly comprises includes a bone screw having a threaded shank for engaging a portion of a vertebra and a head portion connected to the threaded shank, a collar with a bottom portion having an opening for receiving a portion of a bone screw and two upwardly extending walls forming a first passage for receiving the rod and forming a second passage for receiving a portion of a wire, a threaded portion, and a threaded closure member threaded for engaging the threaded portion of the collar. In some embodiments, the rod has a non-circular cross-sectional profile, wherein the rod's non-circular cross-sectional profile is complementary to the wire's non-circular cross-sectional profile for engaging the wire to inhibit rotational movement of the rod relative to the wire. In some embodiments, the rod comprises two or more segments. In some embodiments, the method comprises engaging a first segment of a rod to the wire, advancing the first segment along the wire to a second passage in the first collar, engaging a second segment of the rod to the wire, advancing the second segment to a second passage in the second collar, and connecting a leading end of the second segment with the trailing end of the first segment to span a vertebral level with a rod having first and second curvatures.

In some embodiments, each segment of a rod comprises a complementary non-circular cross-sectional profile for engaging the non-circular cross-sectional profile of the wire to inhibit rotational movement of the segment relative to the wire, a surface for engagement with a collar, a leading end for displacing tissue during advancement of a segment along the wire, and a trailing end comprising an engagement feature for connecting with the leading end of an adjacent segment, wherein one or more segments form a rod that can connect to two or more collars to span one or more vertebral levels.

According to another embodiment, the present disclosure includes a method for advancing a rod into a body. The method may include advancing a first bone fastener assembly via a first incision in the body, anchoring the first bone fastener assembly to a first vertebra, advancing a second bone fastener assembly via a second incision in the body, anchoring the second bone fastener assembly to a second vertebra, advancing a wire into the body via a third incision, advancing the wire through transverse openings in the first and second bone fastener assemblies to define a path, advancing the wire out of the body via a fourth incision, engaging a rod with the wire, and advancing the rod through the transverse openings in the first and second bone fastener assemblies along the path. In some embodiments, a bone fastener assembly includes a bone screw having a threaded portion and a head portion coupled to a collar. The collar may have an opening for receiving the head portion of the bone screw and a passage oriented transverse to the opening for receiving the wire or rod or both. In some embodiments, the wire comprises a non-circular cross-sectional profile and the rod comprises a non-circular cross-sectional profile complementary to the wire cross-sectional profile. In some embodiments, the wire maintains the radial orientation of the rod during advancement along the wire. In some embodiments, the rod comprises a passage along a portion thereof. In some embodiments, the step of advancing the rod comprises moving the rod along the wire. In some embodiments, the rod comprises an attachment feature for attaching the rod to the wire. In some embodiments, the step of advancing the rod comprises moving the wire. In some embodiments, the step of advancing the rod comprises advancing the rod from the third incision to the fourth incision. In some embodiments, the step of advancing the rod comprises advancing the rod from the fourth incision to the third incision. In some embodiments, the rod comprises two segments, wherein each segment comprises a surface for engagement with a collar, a leading end for displacing tissue during advancement through the body, and a trailing end comprising a connection feature for connecting with an adjacent segment, wherein connecting the two segments forms a rod, wherein engaging the two connected segments to the two bone fastener assemblies spans a vertebral level.

Embodiments disclosed herein provide many advantages. For example, in embodiments of the spine stabilization system and method disclosed herein, a spinal rod is not confined to a fixed arc during insertion.

Yet another advantage provided by embodiments of the spine stabilization system and method disclosed herein is that the additional components used for percutaneous delivery of a spinal rod can be easy to place and use.

BRIEF DESCRIPTION OF THE FIGURES

Additional features and advantages of the embodiments will become apparent to those skilled in the art with the benefit of the following detailed description and upon reference to the accompanying drawings in which:

FIGS. 1 and 2 depict perspective views of embodiments of a portion of a spine stabilization system.

FIG. 5 depicts a front view of one embodiment of a bone fastener assembly with a collar that allows for angulation of a bone fastener relative to the collar in a conical range of motion that is symmetrical relative to an axis that passes through a central axis of the collar and a central axis of a bone fastener.

FIG. 6A depicts a front view of one embodiment of a bone fastener assembly with a collar that allows for angulation of a bone fastener relative to the collar in a conical range of motion that is not symmetrical relative to an axis that passes through a central axis of the collar and a central axis of a bone fastener. The collar allows additional lateral bias relative to a non-biased collar.

FIG. 6B depicts a side view of one embodiment of a bone fastener assembly with a collar that allows for angulation of a bone fastener relative to the collar in a conical range of motion that is not symmetrical relative to an axis that passes through a central axis of the collar and a central axis of a bone fastener. The collar allows additional caudal or cephalid bias relative to a non-biased collar.

FIG. 8 depicts a perspective view of one embodiment of a targeting needle.

FIG. 9 depicts a perspective view of an outer housing of a targeting needle.

FIG. 10 depicts a perspective view of one embodiment of a member of a targeting needle.

FIG. 11 depicts a perspective view of one embodiment of a guide wire.

FIG. 12 depicts a perspective view of one embodiment of a guide wire.

FIG. 21 depicts a partial cross-sectional view of one embodiment of a sleeve with an inner sleeve.

FIG. 22 depicts a partial cross-sectional representation of one embodiment of a sleeve coupled to a collar of a bone fastener assembly.

FIG. 23 depicts a partial cross-sectional representation of one embodiment of a sleeve coupled to a collar of a bone fastener assembly.

FIG. 24 depicts a partial cross-sectional representation of one embodiment of a sleeve coupled to a collar of a bone fastener assembly.

FIGS. 39A and 39B depict perspective views of a tool designed to position a closure member in a collar coupled to a bone fastener.

FIGS. 40A and 40B depict perspective views of a tool designed to position a closure member in a collar coupled to a bone fastener.

FIGS. 44A-44E depict schematic views of guide wire placement during a minimally invasive spine stabilization procedure.

FIGS. 47A-47D depict schematic views of insertion of a sleeve and bone fastener assembly during a minimally invasive spine stabilization procedure.

FIGS. 52A-52D depict schematic views of a sleeve removal during a minimally invasive spine stabilization procedure.

Figure 3:
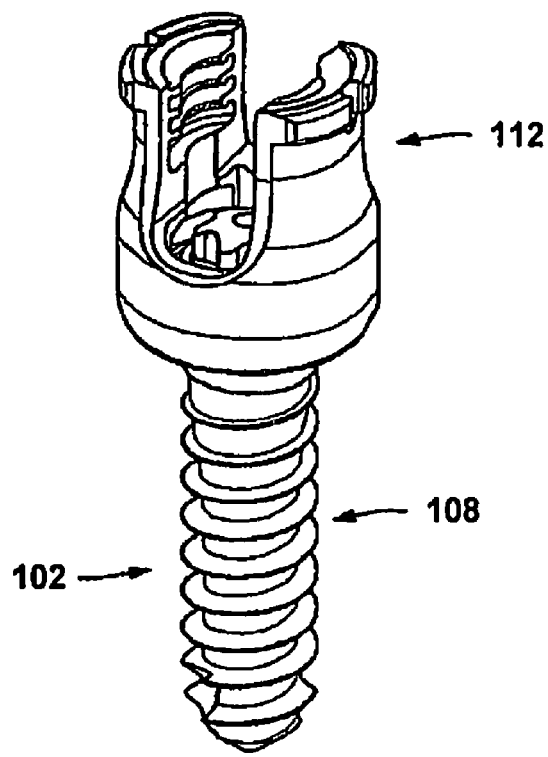
FIG. 3 depicts a perspective view of one embodiment of a portion of a bone fastener assembly.

Specific embodiments are shown by way of example in the drawings and will herein be described in detail. The drawings may not be to scale. It should be understood that the drawings and detailed description thereto are not intended to limit the embodiments to the particular form disclosed.

DETAILED DESCRIPTION OF THE DISCLOSURE

A spine stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spine stabilization system may be installed using a minimally invasive procedure. An instrumentation set may include instruments and spine stabilization system components for forming a spine stabilization system in a patient.

A minimally invasive procedure may be used to limit an amount of trauma to soft tissue surrounding vertebrae that are to be stabilized. Particularly, a procedure may be used to percutaneously deliver a spinal rod. In some embodiments, the natural flexibility of skin and soft tissue may be used to limit the length and/or depth of an incision or incisions needed during the stabilization procedure. Minimally invasive procedures may provide limited direct visibility in vivo. Forming a spine stabilization system using a minimally invasive procedure may include using tools to position system components in the body. A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spine stabilization system. A minimally invasive procedure for stabilizing the spine may be performed without prior insertion of one or more spinal implants in some patients. In some patients, a minimally invasive procedure may be used to install a spine stabilization system after one or more spinal implants are inserted using a posterior spinal approach. A spine stabilization system may be used to achieve rigid pedicle fixation while minimizing the amount of damage to surrounding tissue. In some embodiments, a spine stabilization system may be used to provide stability to two adjacent vertebrae (i.e., one vertebral level). A spine stabilization system may include two bone fastener assemblies. One bone fastener assembly may be positioned in each of the vertebrae to be stabilized. A wire may be advanced to the bone fastener assemblies. A rod may be advanced along the wire and coupled and secured to the bone fastener assemblies. As used herein, "coupled" components may directly contact each other or may be separated by one or more intervening members. In some embodiments, a single spine stabilization system may be installed in a patient. Such a system may be referred to as a unilateral, single-level stabilization system or a single-level, two-point stabilization system. In some embodiments, two spine stabilization systems may be installed in a patient on opposite sides of a spine. Such a system may be referred to as a bilateral, single-level stabilization system or a single-level, four-point stabilization system.

In some embodiments, a spine stabilization system may provide stability to three or more vertebrae (i.e., two or more vertebral levels). In a two vertebral level spine stabilization system, the spine stabilization system may include three bone fastener assemblies. One bone fastener assembly may be positioned in each of the vertebrae to be stabilized. A wire may be advanced through an incision and passed through the bone fastener assemblies. A rod may be advanced along the wire and coupled and secured to the three bone fastener assemblies. In some embodiments, a single two-level spine stabilization system may be installed in a patient. Such a system may be referred to as a unilateral, two-level stabilization system or a two-level, three-point stabilization system. In some embodiments, two three-point spine stabilization systems may be installed in a patient on opposite sides of a spine. Such a system may be referred to as a bilateral, two-level stabilization system or a two-level, six-point stabilization system. In some embodiments, combination systems may be installed. For example, a two-point stabilization system may be installed on one side of a spine, and a three-point stabilization system may be installed on the opposite side of the spine. The composite system may be referred to a five-point stabilization system. Minimally invasive procedures may reduce trauma to soft tissue surrounding vertebrae that are to be stabilized. Only small openings may need to be made in a patient. For example, for a single-level stabilization procedure on one side of the spine, the surgical procedure may be performed through four small incisions formed in the skin of the patient.

Components of spine stabilization systems may be made of materials including, but not limited to, titanium, titanium alloys, stainless steel, ceramics, and/or polymers. Some components of a spine stabilization system may be autoclaved and/or chemically sterilized. Components that may not be autoclaved and/or chemically sterilized may be made of sterile materials. Components made of sterile materials may be placed in working relation to other sterile components during assembly of a spine stabilization system. Spine stabilization systems may be used to correct problems in lumbar, thoracic, and/or cervical portions of a spine. Various embodiments of a spine stabilization system may be used from the C1 vertebra to the sacrum. For example, a spine stabilization system may be implanted posterior to the spine to maintain distraction between adjacent vertebral bodies in a lumbar portion of the spine.

Recently, it has become increasingly popular to insert spinal fixation rods percutaneously. One existing system is a sextant or tripod that delivers a fixation rod via a fixed trajectory along a fixed arc (i.e., such systems have a fixed pivot point). One problem is that such systems do not easily accommodate procedures in which the spinal curvature does not easily align along an arc achievable by the sextant.

Embodiments of the present disclosure may be used in a wide variety of medical applications where the minimally invasive implantation of a rod may be desirable. The systems and methods described herein may find utility in medical procedures where it is desirable to construct a spine fixation system having selected curvature.

FIG. 1 illustrates one embodiment of a portion of a spine stabilization system, which comprises bone fastener assembly 102 and rod 104 (shown in a cross-sectional view). As will be described below in more detail, wire 400 (shown in a cross-sectional view in conjunction with rod 104) is useful for the percutaneous advancement of rod 104 into the body and through collar 112 of bone fastener assembly 102 for constructing a spine stabilization system without requiring a sextant. Wire 400 can be formed of titanium, titanium alloys, stainless steel, ceramics, polyethersulfone, PEEK, polymers or other biocompatible material and can be formed as a single piece of material or as multiple pieces that are coupled together. As shown in FIG. 1, wire 400 may have a non-circular cross-sectional profile. Wire 400 may include two or more surfaces 400a-400n. For example, FIG. 1 depicts one embodiment in which wire 400 may have a cross-sectional profile defined by surfaces 400a, 400b, 400c, 400d, 400e, 400f, 400g and 400h. While wire 400 is shown in FIG. 1 as having curved sides with different radiuses of curvature and straight sides of different lengths, wire 400 can have a variety of shapes including, but not limited to, a rectangular profile, a trapezoidal opening, a square profile, an ovoid profile, an egg-shaped profile, a tapered profile, and combinations and/or portions thereof.

Rod 104 may have a cross-sectional profile that is complementary to the cross-sectional profile of wire 400. As shown in FIG. 1, rod 104 may have a cross-sectional profile defined by surfaces 104a, 104b and 104c to enable rod 104 to engage wire 400. Advantageously, the cross-sectional profile of wire 400 may inhibit rotational movement of rod 104 relative to wire 400 so the orientation of rod 104 is maintained during the advancement of rod 104 into the body.

As shown in FIG. 1, collar 112 may have transverse opening 116 for receiving wire 400 and rod 104. In FIG. 1, transverse opening 116 may have a profile that allows wire 400 and/or rod 104 to pass through collar 112 in only one orientation. Advantageously, components of spinal system 100 may be advanced along wire 400 such that they reach collar 112 in a selected orientation.

As shown in FIGS. 1 and 2, opening 116 of collar 112 may have two different sections. A first section, 116A, may be small enough to allow passage of wire 400 only. A second section, 116B may allow passage of wire 400 and rod 104.

In some procedures, it may be desirable to index rod 104 or tools on wire 400. FIG. 2 depicts a perspective view of one embodiment of a portion of spine stabilization system 100 in which rod 104 may be indexed on wire 400. To index rod 104 on wire 400 in FIG. 2, rod 104 may be rotated such that surface 104a contacts any of surfaces 400a-400f. An advantage of this embodiment is the capability to percutaneously construct rod 104 having a desired curvature. Indexing rod 104 on wire 400 may be particularly useful for embodiments in which rod 104 is formed by two or more segments, discussed below.

FIG. 3 depicts one embodiment of bone fastener assembly components. Components of bone fastener assembly 102 depicted in FIG. 3 may include, but are not limited to, bone fastener 108 and collar 112. Bone fastener 108 may be used to anchor bone fastener assembly 102 to a vertebra.

A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments. A bone fastener assembly may be stamped with indicia (i.e., printing on a side of the collar). In some embodiments, a bone fastener assembly or a bone fastener may be color-coded to indicate a length of the bone fastener. In certain embodiments, a bone fastener with a 30 mm thread length may have a magenta color, a bone fastener with a 35 mm thread length may have an orange color, and a bone fastener with a 55 mm thread length may have a blue color. Other colors may be used as desired. Each bone fastener provided in an instrumentation set may have substantially the same thread profile and thread pitch. In one embodiment, the thread may have about a 4 mm major diameter and about a 2.5 mm minor diameter with a cancellous thread profile. In certain embodiments, the minor diameter of the thread may be in a range from about 1.5 mm to about 4 mm or larger. In certain embodiments, the major diameter of the thread may be in a range from about 3.5 mm to about 6.5 mm or larger. Bone fasteners with other thread dimensions and/or thread profiles may also be used. A thread profile of the bone fasteners may allow bone purchase to be maximized when the bone fastener is positioned in vertebral bone.

Bone fastener 108 may include a shank, a head, and a neck. The shank may include threading. In some embodiments, threading may include a self-tapping start. A self-tapping start may facilitate insertion of bone fastener 108 into vertebral bone. The head of bone fastener 108 may include various configurations to engage a driver that inserts the bone fastener into a vertebra. In some embodiments, the driver may also be used to remove an installed bone fastener from a vertebra. In some embodiments, the head may include one or more tool portions. Tool portions may be recesses and/or protrusions designed to engage a portion of the driver. In some embodiments, bone fastener 108 may be cannulated for use in a minimally invasive procedure. The neck of bone fastener 108 may have a smaller diameter than adjacent portions of the head and the shank. The diameter of the neck may fix the maximum angle that the collar of the bone fastener assembly can be rotated relative to bone fastener 108.

In some embodiments, the neck may be sized to allow up to about 40° or more of angulation of the collar relative to the bone fastener. In some embodiments, the neck may be sized to allow up to about 30° of angulation of the collar relative to the bone fastener. In some embodiments, the neck may be sized to allow up to about 20° of angulation of the collar relative to the bone fastener.

As used herein, the term "collar" includes any element that wholly or partially encloses or receives one or more other elements. A collar may enclose or receive elements including, but not limited to, a bone fastener, a closure member, a ring, and/or a rod. In some embodiments, a collar may couple two or more other elements together (e.g., a rod and a bone fastener). A collar may have any of various physical forms. In some embodiments, a collar may have a "U" shape, however it is to be understood that a collar may also have other shapes. A collar may be open or closed. A collar having a slot and an open top, such as collar 112 shown in FIG. 3, may be referred to as an "open collar." A bone fastener assembly that includes an open collar may be referred to as an "open fastener." In some embodiments, a rod may be top loaded into the open fastener. A closure member may be coupled to the collar to secure the rod to the open fastener.

A collar that does not include a slot and an open top, such as depicted in FIGS. 1 and 2, may be referred to as a "closed collar." A spinal implant that includes a closed collar may be referred to as a "closed implant." A closed collar may include an aperture, bore, or other feature in side surfaces for accommodating other components of a stabilization system (e.g., a rod or wire, discussed below). A setscrew may be used to securely couple a rod to a closed implant.

Collar 112 may include a body and arms. The arms may extend from the body. The body of collar 112 may be greater in width than a width across the arms of collar 112 (i.e., the body may have a maximum effective outer diameter greater than a maximum effective outer diameter of the arms). A reduced width across the arms may allow a detachable member to be coupled to the arms without substantially increasing a maximum effective outer diameter along a length of collar 112. Thus, a reduced width across the arms may reduce bulk at a surgical site. A height of collar body may range from about 3 millimeters (mm) to about 7 mm. In one embodiment, a height of the collar body is about 5 mm. The collar body may include an opening in a lower surface. Inner surfaces and/or outer surfaces of collar 112 may be surface treated or include coatings and/or coverings to modify frictional properties or other properties of the collar. Inner surfaces of the arms may include a modified thread. The modified thread may engage a complementary modified thread of a closure member to secure a rod to a bone fastener assembly. The modified thread may have a constant pitch or a variable pitch. A height and a width of the arms may vary. The arms may range in height from about 8 mm to about 15 mm. In one embodiment, a height of the arms is about 11 mm. A width (i.e., effective diameter) of the arms may range from about 5 mm to 14 mm. The arms and the collar body may form a slot. The slot may be sized to receive a rod. A slot may include, but is not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof. In some embodiments, a first portion of the slot may have different dimensions than a second portion of the slot. In certain embodiments, a portion of a slot in the first arm may have different dimensions than a portion of a slot in the second arm.

When rod 104 is positioned in a slot, a portion of rod 104 may contact a head of bone fastener 108 positioned in collar 112. The arms may include ridges or flanges. Flanges may allow collar 112 to be coupled to a detachable member so that translational motion of collar 112 relative to the detachable member is inhibited. Flanges may also include notches. A movable member of a detachable member may extend into a notch. When the movable member is positioned in a notch, a channel in the detachable member may align with a slot in collar 112. With the movable member positioned in a notch, rotational movement of collar 112 relative to the detachable member may be inhibited.

Figure 4:
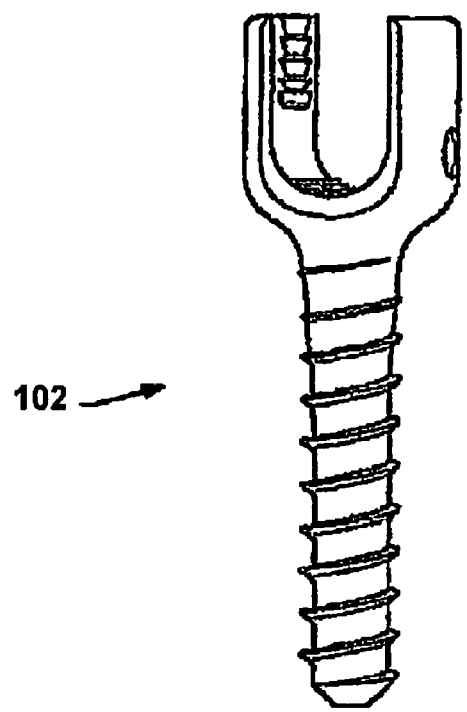
FIG. 4 depicts a side view of one embodiment of a portion of a bone fastener assembly.

In some embodiments, a bone fastener assembly may be a fixed angle fastener. FIG. 4 depicts one embodiment of a fixed angle bone fastener. Collar 112 and bone fastener 108 may be formed as a unitary bone fastener assembly 102. A fixed angle fastener may be positioned as the first bone fastener assembly inserted into a vertebra.

FIG. 5 depicts bone fastener assembly 102 with central axis 158 of collar 112 aligned with central axis 160 of bone fastener 108. Bone fastener 108 may be angulated in a symmetrical conical range of motion characterized by angle α about the aligned axes. Bone fastener 108 may be constrained from motion outside of limit axis 162 by contact between neck 120 of bone fastener 108 and collar 112. Alignment of axis 160 of bone fastener 108 with central axis 158 of collar 112 may be considered a neutral position relative to the range of motion. The alignment is a neutral position because bone fastener 108 may be angulated an equal amount in any direction from central axis 158. When a driver is inserted into bone fastener 108, axis 160 of bone fastener 108 may be substantially aligned with axis 158 of collar 112 to facilitate insertion of the bone fastener into a vertebral body. In certain embodiments, a range of motion of a collar may be skewed from a full conical range of motion relative to aligned central axes of the collar and a bone fastener coupled to the collar. In some embodiments, a distal end of a collar may be shaped to skew, or bias, the range of motion from the range of motion depicted in FIG. 8.

FIGS. 6A and 6B depict bone fastener assemblies 102 with biased collars 112. Body 140 of biased collar 112 may be shaped to restrict relative movement of bone fastener 108 (and/or the collar) to a skewed conical range of motion defined by limit axes 162. As depicted by limit axes 162 in FIG. 6A, a first arm 142 of collar 112 may approach bone fastener 108 more closely than a second arm of the collar. Similarly, as suggested by limit axes 162 in FIG. 6B, collar 112 may be oriented such that the slot formed by arms 142 may not be parallel (e.g., an opening on one side of collar 112 may be higher than a second opening on the other side). Other biased collars may be designed to selectively restrict relative movement of collars and/or bone fasteners. In some embodiments, a biased collar may be attached to a detachable member such that a surgeon performing a minimally invasive procedure may selectively align the portion of the collar with the greater range of motion as needed. For example, the collar depicted in FIGS. 6A-6B may be coupled to a single-level (e.g., C-shaped) sleeve so that the side of the collar (i.e., the side of the slot) with a larger range of motion is positioned next to a channel opening of the sleeve.

When a biased collar of a bone fastener assembly is coupled to a detachable member and a drive mechanism is coupled to a bone fastener of the bone fastener assembly, central axis 158 of collar 112 may align with central axis 160 of bone fastener 108 to facilitate insertion of the bone fastener into bone. In some embodiments, the bias of the collar may be so large that a flexible drive member is needed to drive the bone fastener into bone. In some embodiments, one or more biased collars may be used in a spine stabilization system. The spine stabilization systems may be single-level systems or multi-level systems. Biased collars may be used to accommodate the increasing angle of the pedicle corridor for each lumbar vertebra. The angle may increase by about five degrees for each successive lumbar vertebra.

Figure 7A:
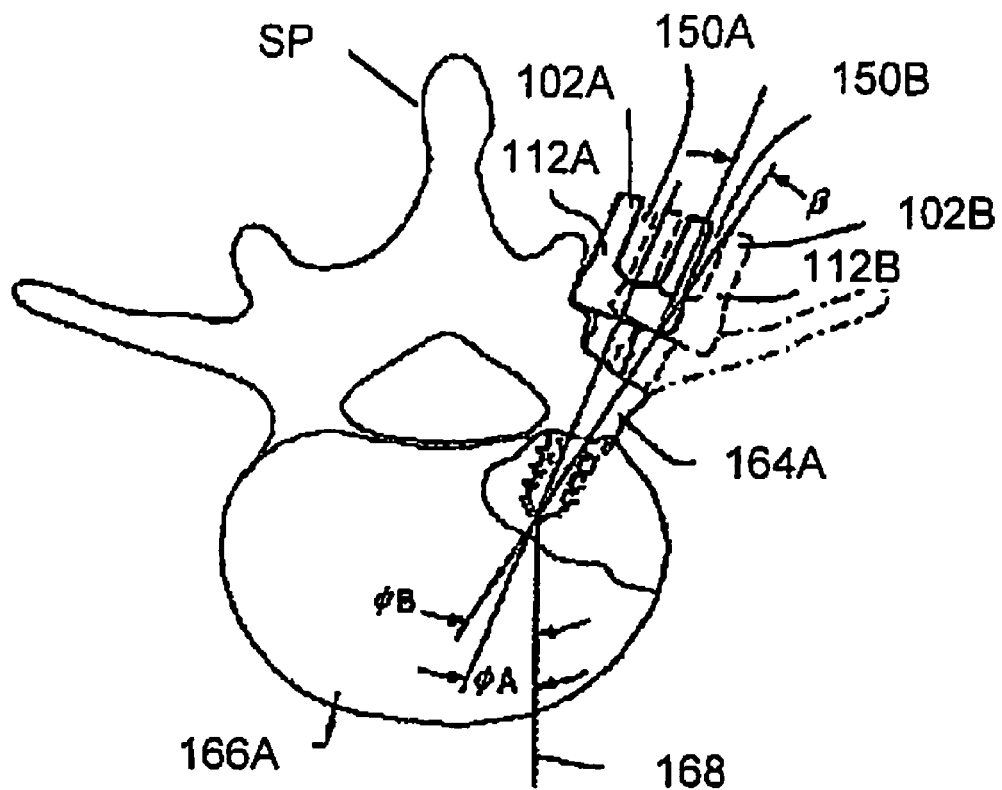
FIG. 7A depicts a schematic side view representation of embodiments of bone fastener assemblies positioned in vertebrae.
Figure 7B:
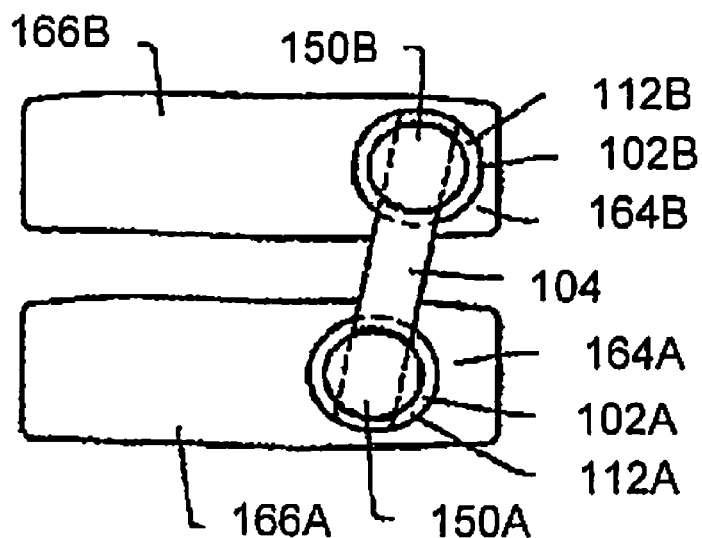
FIG. 7B depicts a schematic top view representation of one embodiment of a single-level spine stabilization system.

FIGS. 7A and 7B depict inferior and posterior views of a single-level spine stabilization system including bone fastener assembly 102A coupled to pedicle 164A and vertebra 166A and bone fastener assembly 102B coupled to pedicle 164B and vertebra 166B. A bone fastener of bone fastener assembly 102A may engage pedicle 164A at pedicle angle φA relative to sagittal plane 168. Pedicle angle φA may range between about 13° and about 17°. Collar 112A of bone fastener assembly 102A may be unbiased. Pedicle angle φB may range between about 18° and about 22°. Collar 112B may have a bias angle β of about 5°. Bone fastener assembly 102B may engage pedicle 164B at pedicle angle φB. Because the bias of collar 112B is approximately equal to the difference between the pedicle angles of the two vertebrae, slots 150A and 150B in bone fastener assemblies 102A and 102B, respectively, may be generally aligned when both bone fasteners are in neutral positions. Angulation of either or both collars of the bone fastener assemblies may allow fine adjustment of engagement angles of the bone fasteners. In addition, collar angulation may allow adjustment in the orientation of bone fasteners in a sagittal plane (i.e., to conform to lordosis of a spine) while still allowing the collars to be easily coupled with rod 104. Rod 104 may be disposed in slots 150A and 150B and secured by closure members.

In some embodiments, a flexible driver or a polyaxial driver (e.g., a driver with a universal joint) may be used to drive the heads of the bone fasteners from a position that is off axis from the bone fasteners to reduce the size of an opening of the body needed to implant the spine stabilization system. A closure member may be coupled to a collar of a bone fastener assembly to fix a rod positioned in the collar to the bone fastener assembly. In some embodiments, a closure member may be cannulated. In certain embodiments, a closure member may have a solid central core. A closure member with a solid central core may allow more contact area between the closure member and a driver used to couple the closure member to the collar. A closure member with a solid central core may provide a more secure connection to a rod than a cannulated closure member by providing contact against the rod at a central portion of the closure member as well as near an edge of the closure member.

In one embodiment, a bone fastener assembly and a closure member may be coupled with a running fit. A running fit (i.e., a fit in which parts are free to rotate) may result in predictable loading characteristics of a coupling of bone the fastener assembly and the closure member. Predictable loading characteristics may facilitate use of a closure member with a break-off portion designed to shear off at a predetermined torque. A running fit may also facilitate removal and replacement of closure members. In some embodiments, a closure member may include an interference fit (e.g., crest-to-root radial interference). In one embodiment, a position (i.e., axial position and angular orientation) of a modified thread of a collar may be controlled, or "timed," relative to selected surfaces of the collar. For example, a modified thread form may be controlled relative to a top surface of a collar and an angular orientation of the slots of the collar. In some embodiments, positions of engaging structural elements of other coupling systems (e.g., thread forms) may be controlled. Controlling a position of a modified thread form may affect a thickness of a top modified thread portion of a collar. In one embodiment, a position of a modified thread form may be selected such that the thickness of the leading edge of a top modified thread portion is substantially equal to the full thickness of the rest of the modified thread. Controlling a position of a modified thread form of a collar may increase a combined strength of engaged modified thread portions for a collar of a given size (e.g., wall height, modified thread dimensions, and thread pitch). Controlling a position of the modified thread form may reduce a probability of failure of modified thread portions, and thus reduce a probability of coupling failure between a collar and a closure member. Controlling the position of a modified thread form in a collar of a bone fastener assembly may increase a combined strength of engaged collar and closure member modified thread portions such that failure of the modified thread portions does not occur prior to the intended shearing off of a tool portion of the closure member. For example, a tool portion of a closure member may be designed to shear off at about 90 in-lbs of torque, while the combined modified thread portions may be designed to withstand a torque on the closure member of at least 120 in-lbs.

If a thickness of a modified thread portion of a given size and profile is reduced below a minimum thickness, the modified thread portion may not significantly contribute to the holding strength of the modified thread of a collar. In one embodiment, a position of a modified thread form of a collar may be controlled such that a thickness of a top modified thread portion is sufficient for the portion to increase a holding strength of the collar. In one embodiment, a top modified thread portion may have a leading edge thickness of about 0.2 mm. In one embodiment, a position of a modified thread form of a collar may be selected to ensure that a closure member engages a selected minimum number of modified thread portions on each arm of the collar. In one embodiment, at least two modified thread portions having a full thickness over width w of a collar arm may be engaged by a closure member at each arm. Alternatively, a closure member may engage parts of three or more modified thread portions on each arm, with the total width of the portions equal to at least two full-width portions. Allowances may be made for tolerances in the components (e.g., diameter of the rod) and/or anticipated misalignment between the components, such as misalignment between a rod and a slot. In one embodiment, a substantially equal number of modified thread portions in each arm may engage the closure member when a rod is coupled to a bone fastener assembly.

Various instruments may be used in a minimally invasive procedure to form a spine stabilization system in a patient. The instruments may include, but are not limited to, positioning needles, guide wires, dilators, bone awls, bone taps, sleeves, drivers, and mallets. The instruments may be provided in an instrumentation set. The instrumentation set may also include components of the spine stabilization system. The components of the spine stabilization system may include, but are not limited to, bone fastener assemblies of various sizes and/or lengths, rods, and closure members. Instruments used to install a spine stabilization system may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

A targeting needle may be used to locate an entry point in a vertebral body for a bone fastener of a bone fastener assembly. In some embodiments, the targeting needle may be a bone marrow biopsy needle. FIG. 8 depicts one embodiment of targeting needle 198. Targeting needle 198 may include outer housing 200 and member 202.

FIG. 9 depicts one embodiment of outer housing 200. Outer housing 200 may include hollow shaft 204 and handle 206. Scale markings 208 may be printed, etched, or otherwise placed on hollow shaft 204. Scale markings 208 may be used to approximate a length of a bone fastener needed for a vertebra. Handle 206 may provide a grip that allows a user to manipulate the targeting needle. Handle 206 may include threaded portion 210. Threaded portion 210 may couple to threading on a portion of a targeting needle member to secure the member to outer housing 200.

FIG. 10 depicts one embodiment of member 202 of a targeting needle. Member 202 may include point 212 and cap 214. Point 212 may be placed through a hollow shaft of an outer housing of the targeting needle. Cap 214 may include threading 216. Member 202 may be rotated relative to the outer housing to couple threading 216 with threading in a handle of the outer housing. In some embodiments, the member may be coupled to the outer housing by another type of connection system (e.g., by placement of a key in a keyway). With member 202 positioned in an outer housing, point 212 may extend from a distal end of a hollow shaft of the outer housing. Cap 214 may be used as an impact surface for driving the targeting needle in bone.

FIG. 11 and FIG. 12 depict embodiments of guide wire 218. Guide wire 218 may be an 18-gauge K-wire. Guide wire 218 may pass down a shaft of a targeting needle outer housing. Guide wire 218 may be from about 15 cm to about 65 cm in length. In some embodiments, guide wires 218 provided in an instrumentation set are about 46 cm in length. The length of guide wire 218 may allow a surgeon and/or assistants to hold at least one portion of guide wire 218 at all times when guide wire 218 is inserted into vertebral bone, even during insertion, use, and removal of instruments along a length of guide wire 218. Guide wire 218 that can be held continuously during a surgical procedure may inhibit removal or advancement of guide wire 218 from a desired position during a minimally invasive surgical procedure.

As depicted in FIG. 11, a distal end of guide wire 218 may include point 220. Point 220 may facilitate insertion of the distal end of guide wire 218 into vertebral bone. As depicted in FIG. 12, a distal end of guide wire 218 may not be pointed. A position of an unpointed guide wire 218 in bone may be easier to maintain during a spine stabilization procedure.

Dilators may be used during a minimally invasive surgical procedure to push aside tissue and create space to access vertebral bone. In some embodiments, four tissue dilators of increasing diameter may be used to establish sufficient working space to accommodate instruments and spine stabilization system components. In some embodiments, especially for a mid-vertebra or for mid-vertebrae of a multi-level stabilization system, only three dilators may be needed to form sufficient working space. Dilators in an instrumentation set may increase in diameter incrementally by a selected amount. For example, outside diameters of dilators in an instrumentation set may increase sequentially by increments of about 0.5 mm.

A detachable member for a single-level vertebral stabilization system may include one or more channels in a wall of the detachable member to allow access to an adjacent vertebra. For some single-level vertebral stabilization procedures, only single-channel detachable members (i.e., detachable members with a single channel in a wall of the detachable member) may be used. For other single-level vertebral stabilization procedures, one or more multi-channel detachable members (i.e., detachable members with two or more channels in a wall of the detachable member) may be used. Channels may provide flexibility to or enhance flexibility of a multi-channel detachable member. In some embodiments, a proximal portion of a multi-channel detachable member may have a solid circumference. A region of solid circumference in a multi-channel detachable member may enhance stability of the multi-channel detachable member. In some embodiments, a multi-channel detachable member may be longer than a single-channel detachable member.

A detachable member used at a middle vertebra in a multi-level stabilization procedure may be a multi-channel detachable member. Channels in a multi-channel detachable member may allow access to adjacent vertebrae from a middle vertebra. A detachable member used at an end vertebra of a multi-level stabilization system may be a single-channel detachable member or a multi-channel detachable member. A system for coupling a bone fastener assembly to a multi-channel detachable member may include a limiter that inhibits spreading of arms of the detachable member to inhibit release of the bone fastener assembly from the detachable member.

A channel in a wall of a detachable member may allow access to a vertebra that is to be stabilized with a spine stabilization system being formed. In some embodiments, a single-channel detachable member may be coupled to a bone fastener assembly to be inserted into vertebral bone of a first vertebra. The single-channel detachable member may allow access to a second vertebra from the first vertebra. In other embodiments, a multi-channel detachable member may be coupled to a bone fastener assembly to be inserted into vertebral bone of a first vertebra. The multi-channel detachable member may allow access from the first vertebra to adjacent vertebrae.

Instruments may access a bone fastener assembly through a passage in a detachable member. In some embodiments, a channel in a wall of a detachable member may extend a full length of the detachable member. In some embodiments, especially in embodiments of multi-channel detachable members, a channel in a wall of a detachable member may extend only a portion of the length of the detachable member. In some embodiments, a channel in a wall of a detachable member may extend 25%, 50%, 75%, 80%, 90%, 95% or more of the length of the detachable member.

A channel in a detachable member may be any of a variety of shapes. In some embodiments, a channel may be a linear opening parallel to a longitudinal axis of the detachable member. In some embodiments, a channel may have a non-linear shape including, but not limited to, a helical pattern, an arc, an "L" shape, or an "S" shape.

Movable members may extend through portions of a detachable member proximate a channel in the detachable member. Movable members may engage notches in a collar to establish a radial orientation of the detachable member on the collar and/or to inhibit rotation of the collar relative to the detachable member. A distal end of a movable member may be flat, curved, or angled. In some embodiments, a distal end of a movable member may be threaded. In other embodiments, a distal end of a movable member may be a projection that engages an opening in a collar. In some embodiments, an upper surface of a collar and/or a surface of a distal end of a movable member may be textured to inhibit rotation of the collar relative to the detachable member. In certain embodiments, a proximal end of a movable member may include a tool engaging portion. A tool engaging portion may include, but is not limited to, a hex section, a hexalobular section, a tapered section, a bead, a knot, a keyed opening, a coating, a threading, and/or a roughened surface for engaging a drive that rotates or otherwise displaces the movable member.

A cross section transverse to a longitudinal axis of a detachable member may have shapes including, but not limited to, circular, ovoid, square, pentagonal, hexagonal, and combinations thereof. In some embodiments, a detachable member may be hollow. In certain embodiments, a thickness of a hollow detachable member may be uniform. In certain embodiments, a thickness of a hollow detachable member may vary along the length of the detachable member. A detachable member with a passage extending longitudinally from a first end of the detachable member to a second end of the detachable member may be referred to as a "sleeve".

Figure 13:
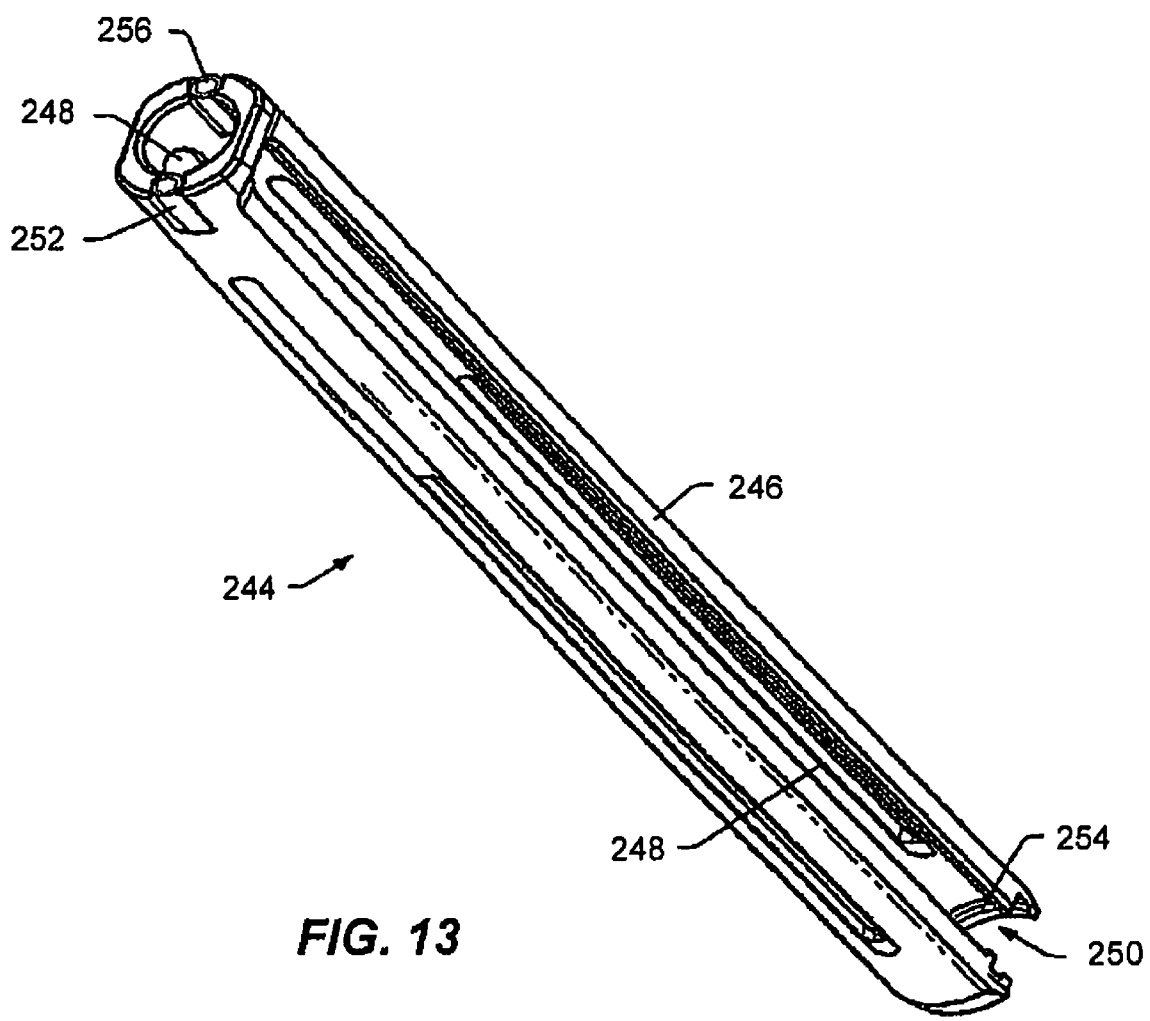
FIG. 13 depicts a perspective view of one embodiment of a multi-channel sleeve.

FIG. 13 depicts one embodiment of sleeve 244. Sleeve 244 may be a multi-channel sleeve. Sleeve 244 may include wall 246, channels 248, passage 250, movable members 252, and flange 254. Channels 248 may extend from a distal end of sleeve 244 through a portion of wall 246. Passage 250 may allow instruments to be positioned and used to manipulate a bone fastener assembly that is coupled to a distal end of sleeve 244. Movable members 252 may be part of a system that couples a bone fastener assembly to sleeve 244. In some embodiments, movable members 252 may include tool engaging portion 256. A driver may be positioned in tool portion 256. The driver (e.g., a hex wrench) may be used to extend or retract a distal end of movable member 252. A distal end of sleeve 244 may include flange 254 that mates with a complementary flange on a collar of a bone fastener assembly. A distal end of sleeve 244 may be tapered to reduce bulk (e.g., reduce spin diameter) at a surgical site.

Figure 14:
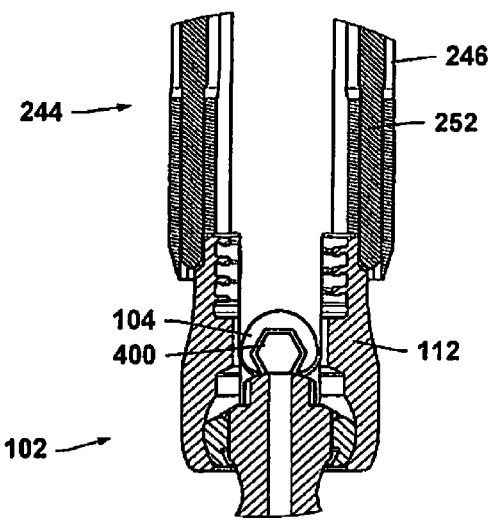
FIG. 14 depicts a cross-sectional representation of a portion of the sleeve with the bone fastener assembly taken substantially along line 14-14 of FIG. 13.

FIG. 14 depicts a cross-sectional representation of a portion of sleeve 244 with bone fastener assembly 102 and rod 104. Distal ends of movable members 252 may extend into notches in collar 112. Portions of walls 246 of sleeve 244 may include threading. Portions of movable members 252 may include threading complementary to threaded portions of walls 246. Threading of movable members 252 may engage threading in walls 246 such that rotation of the movable members advances or retracts the movable members relative to the walls.

As shown in FIG. 14, collar 112 may be designed such that rod 104 lies below a distal end of sleeve 244. Coupling sleeve 244 to collar 112 above rod 104 may reduce bulk at a surgical site. With rod 104 coupled to collar 112 below a distal end of sleeve 244, the sleeve may be removed without interference from the rod of a spine stabilization system.

Figure 15:
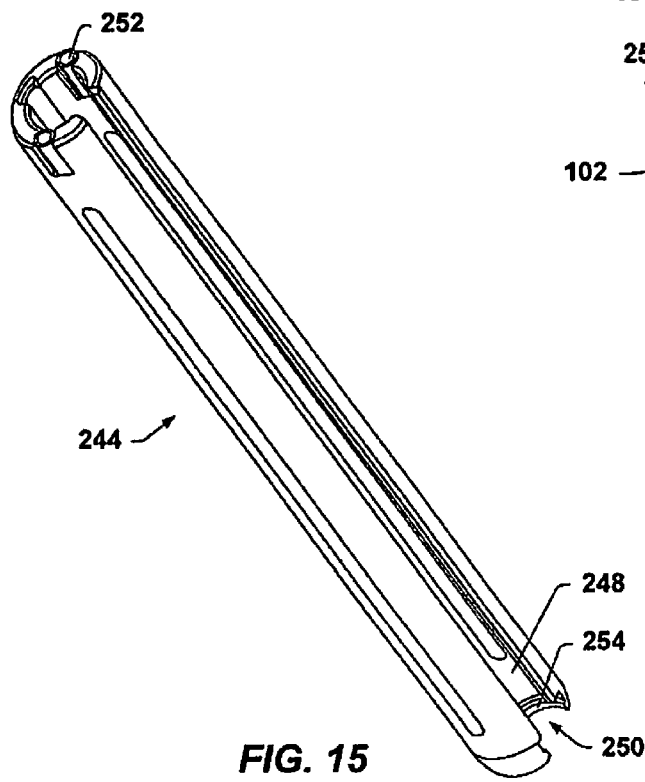
FIG. 15 depicts a perspective view of one embodiment of a single-channel sleeve.

FIG. 15 depicts one embodiment of sleeve 244. Sleeve 244 may be a single-channel sleeve for use in single-level or multi-level spine stabilization procedures. Sleeve 244 may be used at the outermost vertebrae to be stabilized during installation of a multi-level vertebral stabilization system. Sleeve 244 may be coupled to a collar of a bone fastener assembly with movable members 252 and/or flange 254. Instruments may be inserted through passage 250 of sleeve 244 to access an anchored bone fastener assembly coupled to the sleeve.

A sleeve may be coupled to a bone fastener assembly in various ways to inhibit movement of the sleeve relative to a collar of the bone fastener assembly. A system used to couple the sleeve to the bone fastener assembly may inhibit rotation and translation of the sleeve relative to the collar.

A detachable member may be coupled to a collar of a bone fastener assembly in various ways. When a detachable member is coupled to a collar, rotation and translation of the detachable member relative to the collar may be inhibited. A system used to couple a detachable member and collar should be simple, inexpensive to implement, and should not significantly weaken the mechanical strength of the collar and/or the detachable member. Detachable members may be coupled to collars using various coupling systems including, but not limited to, flanges, threaded connections, interlocking connections (e.g., ratcheting connection systems), and/or interference fits.

In one embodiment of an interlocking connection system, a detachable member may include an opposing pair of deflectable arms. Each deflectable arm may include a tooth. The deflectable arms may be forced outwards during coupling of a collar to the detachable member. When the collar is coupled to the detachable member, the deflectable arms may be positioned in channels in the collar, with the teeth positioned in indentions in the collar. The presence of the deflectable arms in the channels of the collar may inhibit rotation and translation of the detachable member relative to the collar. Separation of the detachable member from the collar may be achieved by insertion of an expander in the detachable member. The expander may be used to force the deflectable arms outwards and expel the teeth from the indentions.

FIGS. 16-26 depict embodiments of sleeves coupled to bone fastener assemblies. In each bone fastener assembly/sleeve embodiment depicted in FIGS. 16-24 and FIG. 26, rod 104 and wire 400 positioned in collar 112 of bone fastener assembly 102 would lie below distal end 427 of sleeve 244. In some embodiments, seating rod 104 may be accomplished by advancing rod 104 over a wire (e.g., See FIG. 37 described below). Having rod 104 and wire 400 below the distal end of sleeve 244 reduces bulk at the surgical site. With sleeve 244 positioned above rod 104, interference of the secured rod 104 or wire 400 with sleeve 244 is avoided during removal of sleeve 244.

Figure 16:
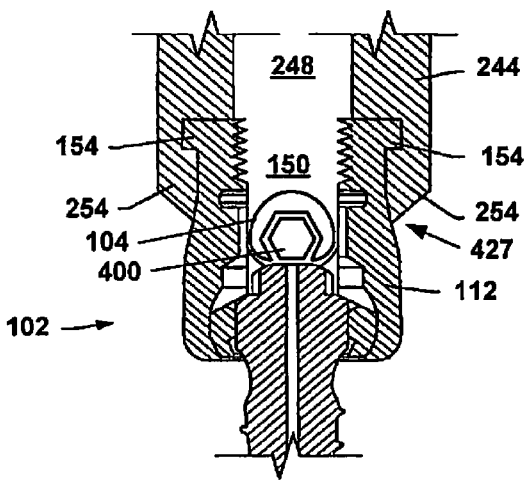
FIG. 16 depicts a partial cross-sectional representation of one embodiment of a sleeve coupled to a collar of a bone fastener assembly.

FIG. 16 depicts a cross-sectional representation of sleeve 244 including sleeve flange 254. Sleeve 244 may be rotated onto collar 112 until slot 150 aligns with channel 248. Sleeve flange 254 may engage flange 154 of collar 112 to inhibit translation of sleeve 244 relative to collar 112 of bone fastener assembly 102. Wire 400 and rod 104 may be advanced through slot 150 and positioned in collar 112 below distal end 427 of sleeve 244.

In some detachable member and collar coupling embodiments, the detachable member and the collar may include members that work together to inhibit radial expansion of walls of the detachable member. In some detachable member and collar coupling embodiments, a detachable member may include a protrusion that mates with a complementary groove in a collar. Alternatively, a detachable member may include a groove that mates with a complementary protrusion of a collar.

In some embodiments, a detachable member and/or a collar may include a locking system to inhibit rotation of the detachable member relative to the collar. The locking system may be, but is not limited to, threading, interference fits, frictional engagement, or a press-fit connection. In some embodiments, a locking system may inhibit translation and/or rotation of a detachable member relative to a collar.

Figure 17:
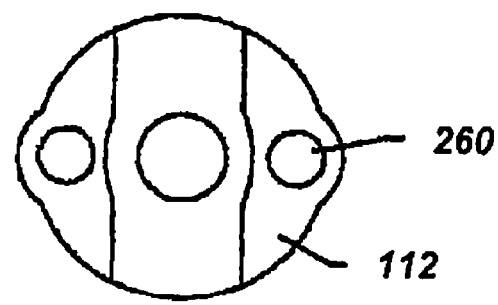
FIG. 17 depicts top view representation of one embodiment of a collar.

FIG. 17 depicts a top view representation of one embodiment of collar 112 of a bone fastener assembly. Collar 112 includes openings 260. In some embodiments, openings 260 may be threaded. In some embodiments, openings 260 may not include threading. The body of collar 112 adjacent to openings 260 may include extra material to provide strength to the collar.

Figure 18:
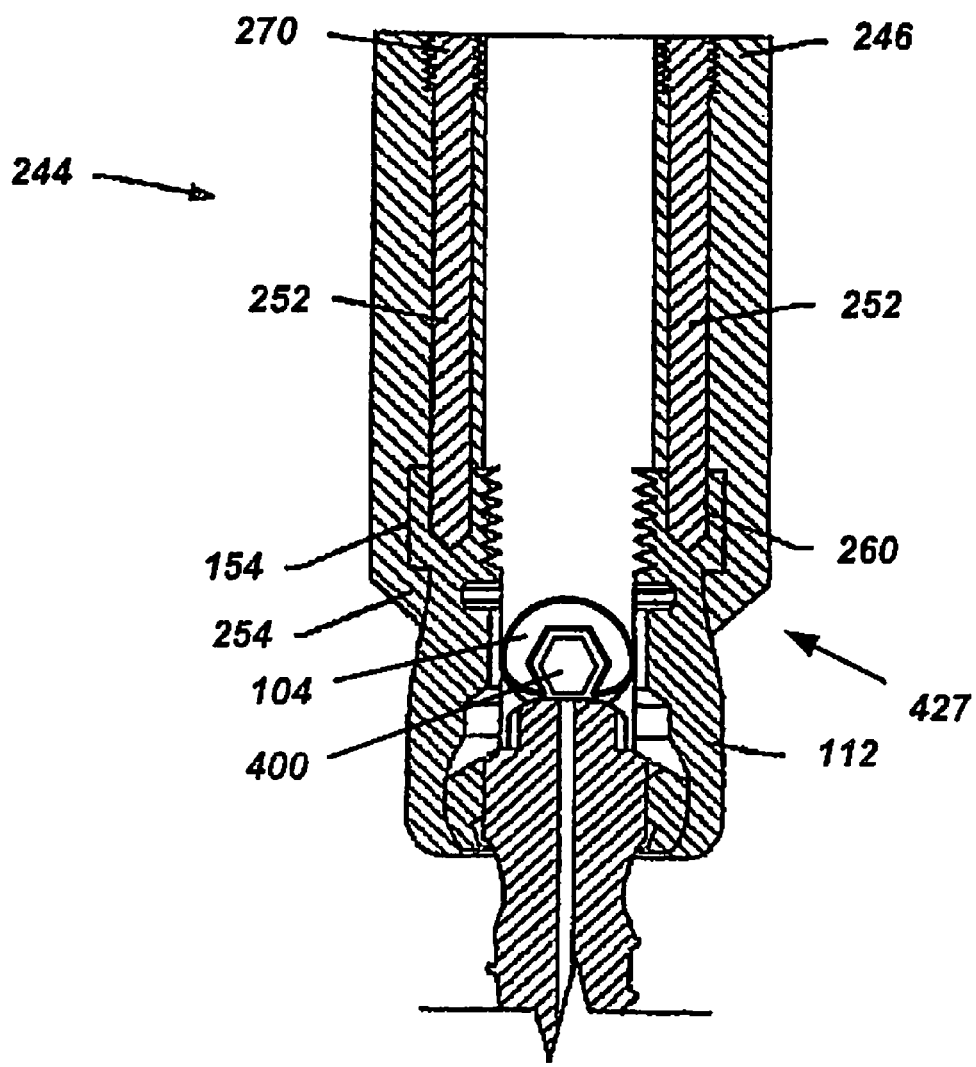
FIG. 18 depicts a partial cross-sectional representation of one embodiment of a sleeve coupled to one embodiment of a collar of a bone fastener assembly, such as the collar depicted in FIG. 17.

FIG. 18 depicts a partial cross-sectional representation of one embodiment of sleeve 244 coupled to one embodiment of collar 112, such as collar 112 depicted in FIG. 18. Distal end portions of movable members 252 may extend into openings 260. When distal end portions of movable members 252 are positioned in openings 260, rotational movement of sleeve 244 relative to collar 112 may be inhibited. Sleeve 244 may include flange 254. Flange 254 may engage flange 154 of collar 112 to inhibit translation of sleeve 244 relative to the collar. In one embodiment in which distal end portions of movable members in a sleeve are threaded and openings in the collar are threaded, rotation and translation of the collar relative to the sleeve may be inhibited when distal end portions of the movable members are positioned in the openings. Wire 400 and rod 104 may be advanced through slot 150 in collar 112 and positioned below distal end of sleeve 244. As depicted in FIG. 18, portion 270 of movable member 252 may include threading. Threading of portion 270 may engage threading in wall 246 of sleeve 244. Engagement of threading of portion 270 with threading in wall 246 may allow distal end portion of movable member 252 to advance towards, or retract from, a distal end of sleeve 244 when the movable member is rotated.

Figure 19:
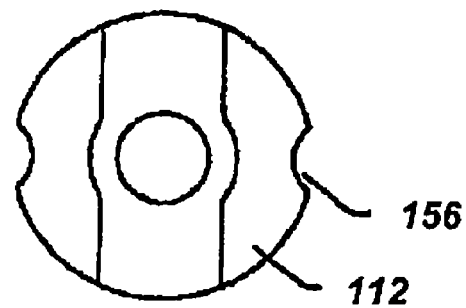
FIG. 19 depicts a top view representation of one embodiment of a collar.
Figure 20:
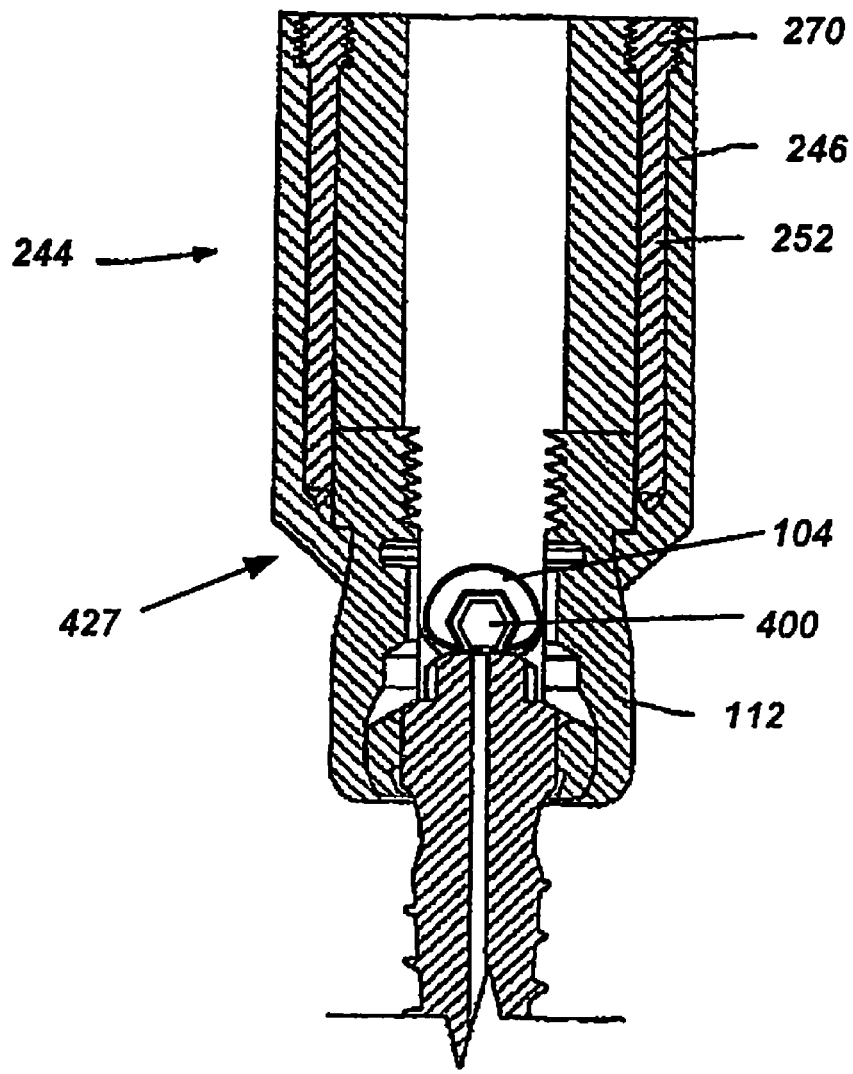
FIG. 20 depicts a partial cross-sectional representation of one embodiment of a sleeve coupled to one embodiment of a collar of a bone fastener assembly, such as the collar depicted in FIG. 19.

FIG. 19 depicts a top view representation of one embodiment of collar 112 of a bone fastener assembly. Collar 112 may include notches 156. FIG. 20 depicts a partial cross-sectional representation of one embodiment of sleeve 244 coupled to one embodiment of collar 112, such as the collar depicted in FIG. 19. Distal end portions of movable members 252 of sleeve 244 may be extended and positioned in notches 156 of collar 112. An interference fit between the distal end portions of movable members 252 and the body of collar 112 that defines the notches may inhibit rotation of sleeve 244 relative to the collar. Wire 400 and rod 104 may be advanced through slot 150 in collar 112 and positioned below distal end of sleeve 244.

Portion 270 of movable member 252 may include threading. Threading of portion 270 may engage threading in wall 246 of sleeve 244. Engagement of threading of portion 270 with threading in wall 246 may allow a distal end portion of movable member 252 to advance towards, or retract from, a distal end of sleeve 244 when the movable member is rotated.

In one embodiment, an inner sleeve may be positioned in a sleeve to inhibit translation and/or rotation of the sleeve relative to a collar of a bone fastener assembly. FIG. 21 depicts a cross-sectional view of sleeve 244 with inner sleeve 272. A distal end of inner sleeve 272 may contact an upper end of collar 112. A proximal portion of inner sleeve 272 may engage a proximal portion of sleeve 244. The engagement may allow inner sleeve 272 to apply a force against collar 112 that presses flange 154 against flange 254 of sleeve 244 to inhibit translation of the sleeve relative to the collar. The engagement may be, but is not limited to, a threaded connection, an interference fit, a frictional fit, or a keyway type of connection. Wire 400 and rod 104 may be advanced through slot 150 in collar 112 and positioned below distal end of sleeve 244.

In some embodiments, a distal end of an inner sleeve may be roughened or textured to frictionally engage a proximal surface of the collar. The frictional engagement may inhibit rotation of the sleeve relative to the collar. In some embodiments, inner sleeve 272 may include passage 274. A pin may pass through passage 274 into an opening in collar 112. When a pin is positioned through passage 274 into the opening, rotation of sleeve 244 relative to collar 112 may be inhibited.

In some embodiments, threading may be used to couple a detachable member to a collar. FIG. 22 and FIG. 23 depict partial cross-sectional representations of sleeves 244 that couple to collars 112 by threaded connections. Sleeves 244 may include female threading that is complementary to male threading of collar 112. In some embodiments, threading of the sleeve and threading of the collar may be modified threads. Wire 400 and rod 104 may be advanced through slot 150 in collar 112 and positioned below distal end of sleeve 244.

FIG. 24 depicts a partial cross-sectional representation of sleeve 244 that couples to collar 112 by a threaded connection. Sleeve 244 may include male threading, and collar 112 may include complementary female threading. Wire 400 and rod 104 may be advanced through slot 150 in collar 112 and positioned below distal end of sleeve 244. In some embodiments, portion 276 of collar 112 that includes threading which mates with threading of sleeve 244 may be a break-off section. Collar 112 may be held in a fixed position. Torque may be applied to sleeve 244 to shear off portion 276.

Figure 25:
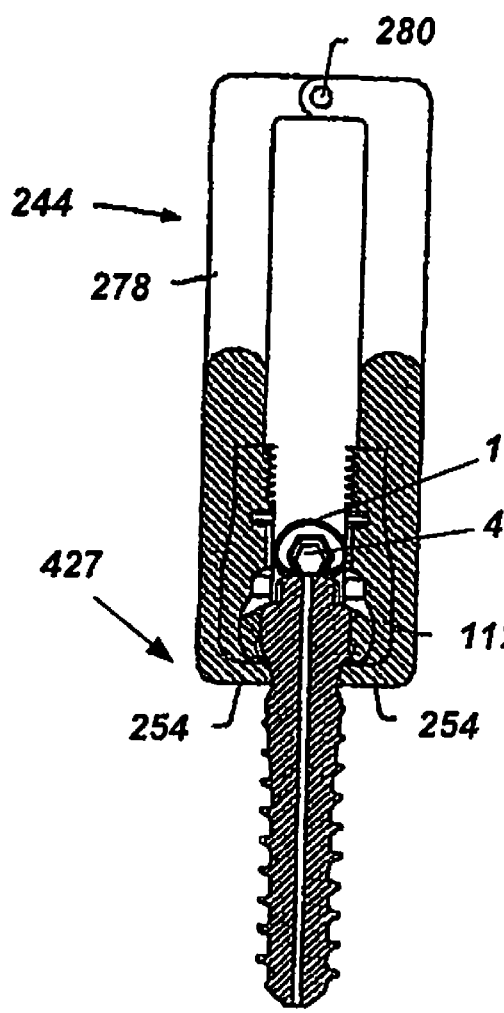
FIG. 25 depicts a cross-sectional representation of one embodiment of a hinged sleeve coupled to a collar of a bone fastener assembly.
Figure 26:
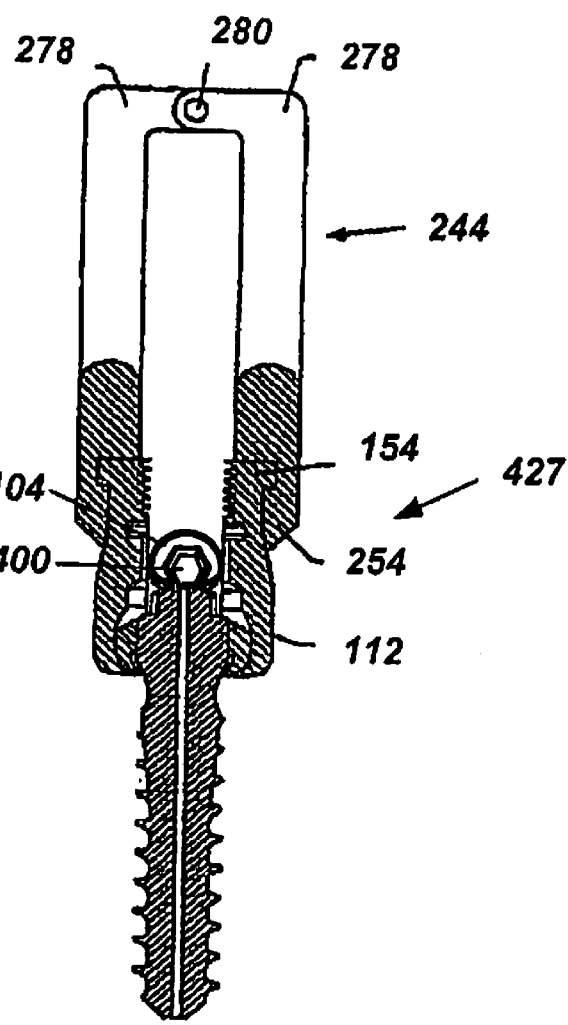
FIG. 26 depicts a cross-sectional representation of one embodiment of a hinged sleeve coupled to a collar of a bone fastener assembly.

In some embodiments, a detachable member may include a pair of hinged arms configured to couple to a collar. FIG. 25 and FIG. 26 depict embodiments of sleeves that include hinged portions. Sleeve 244 may include arms 278. Arms 278 may be pivotally coupled together by hinge 280. Hinge 280 may be located near a proximal end of sleeve 244. In some sleeve embodiments, sleeve 244 may include a locking element or a biasing element (e.g., a spring) near or at hinge 280. A locking element or biasing element may cause a clamping force to be exerted on collar 112 to maintain the collar in the sleeve and/or to inhibit rotation of collar 112 in sleeve 244. In some embodiments, such as in the embodiment depicted in FIG. 25, flange 254 of sleeve 244 may contact a bottom portion of collar 112. Wire 400 and rod 104 may be advanced through slot 150 in collar 112 and positioned above distal end of sleeve 244. In some embodiments, such as in the embodiment depicted in FIG. 26, flange 254 of sleeve 244 may contact flange 154 of collar 112.

In some detachable member embodiments, proximal portions of detachable members may be chamfered to allow ends of the detachable members to more closely approach each other than detachable members with a uniform cross section.

Figure 27:
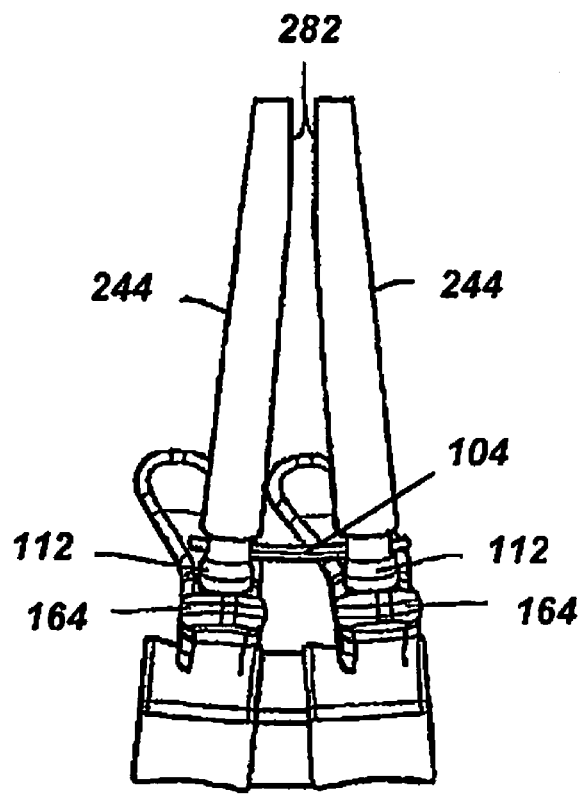
FIG. 27 depicts a schematic representation of sleeve embodiments coupled to collars of a spine stabilization system.

FIG. 27 depicts sleeves 244 coupled to collars 112 engaged in adjacent pedicles 164, and rod 104 having a non-circular cross-sectional profile spanning between collars 112. Sleeves 244 may include chamfered surfaces 282. Chamfered surfaces 282 may reduce space between proximal ends of sleeves 244. During some surgical procedures, only one of the sleeves may be chamfered. During some surgical procedures, the use of a sleeve with a chamfered surface may allow for smaller incisions than required when using non-chamfered sleeves. In some embodiments, other types of detachable members may be used to reduce space between proximal ends of detachable members. Other types of detachable members may include, but are not limited to, detachable members of different lengths, detachable members of different diameters, and detachable members with flexible end portions.

Detachable members may be of various lengths. Detachable members of different lengths may be used in the same surgical procedure. A detachable member length used in a spine stabilization procedure may be determined by a patient's anatomy. Detachable members may be just short enough to allow manipulation by a medical practitioner above an incision in a patient. In some embodiments, detachable members may be about 3.5 to about 11.5 cm long. For example, a single-channel detachable member may be about 10 cm long. In some embodiments, detachable members may be about 11.5 cm to about 14 cm long. For example, a single-channel or a multi-channel detachable member may be about 12.5 cm long. A multi-channel detachable member may be longer than a single-channel detachable member. In some embodiments, a multi-channel detachable member may be at least about 15 cm long. For example, a multi-channel detachable member may be about 16 cm long. Detachable members that are too long may require a longer incision and/or a larger tissue plane for insertion of a spine stabilization system. Insertion of a rod may be more difficult with detachable members that are longer than necessary. Detachable members with excess length may be bulky and hard to manipulate during a surgical procedure.

A detachable member may be flexible over its entire length or include a flexible portion near a proximal end of the detachable member. A flexible portion may allow positioning of a proximal portion of a detachable member in a desired location. A flexible portion may be produced from any of various materials including, but not limited to, a surgical grade plastic, rubber, or metal. A flexible portion may be formed of various elements, including, but not limited to, a tube, a channel, or a plurality of linked segments.

Figure 28:
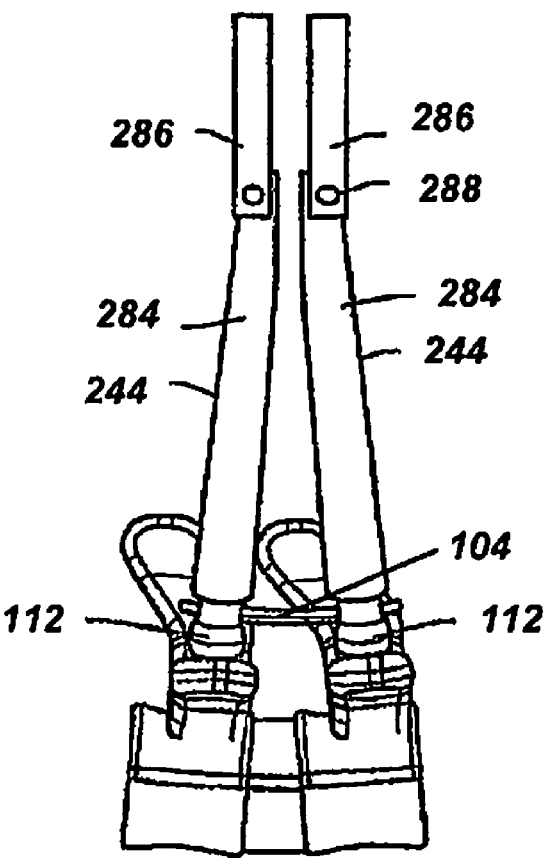
FIG. 28 depicts a schematic representation of sleeve embodiments with connections that allow relative movement of portions of a sleeve.

FIG. 28 depicts one embodiment of sleeves 244 with a connection that allows movement of first portion 284 relative to second portion 286. First portion 284 may be coupled to collar 112 of bone fastener assembly 102, with rod 104 having a non-circular cross-sectional profile spanning between collars 112. Second portion 286 may connect to first portion 284 at linkage 288. Linkage 288 may include, but is not limited to, a locking element, a pivot point, a hinge, or a pin. In some embodiments, the linkage may be a ball and socket type of connection that allows rotational motion of second portion 286 relative to first portion 284. During some spine stabilization procedures, a detachable member without a second portion that is able to move relative to a first portion may be used at one vertebra, and a detachable member with a second portion that is able to move relative to a first portion may be used at one or more vertebrae that are to be stabilized.

When bone fasteners of polyaxial bone fastener assemblies are positioned in vertebral bone, detachable members coupled to collars of the bone fastener assemblies may be moved in desired positions. During surgery, a detachable member in a patient may be oriented towards an adjacent vertebra that is to be stabilized to reduce the required incision size.

Figure 29:
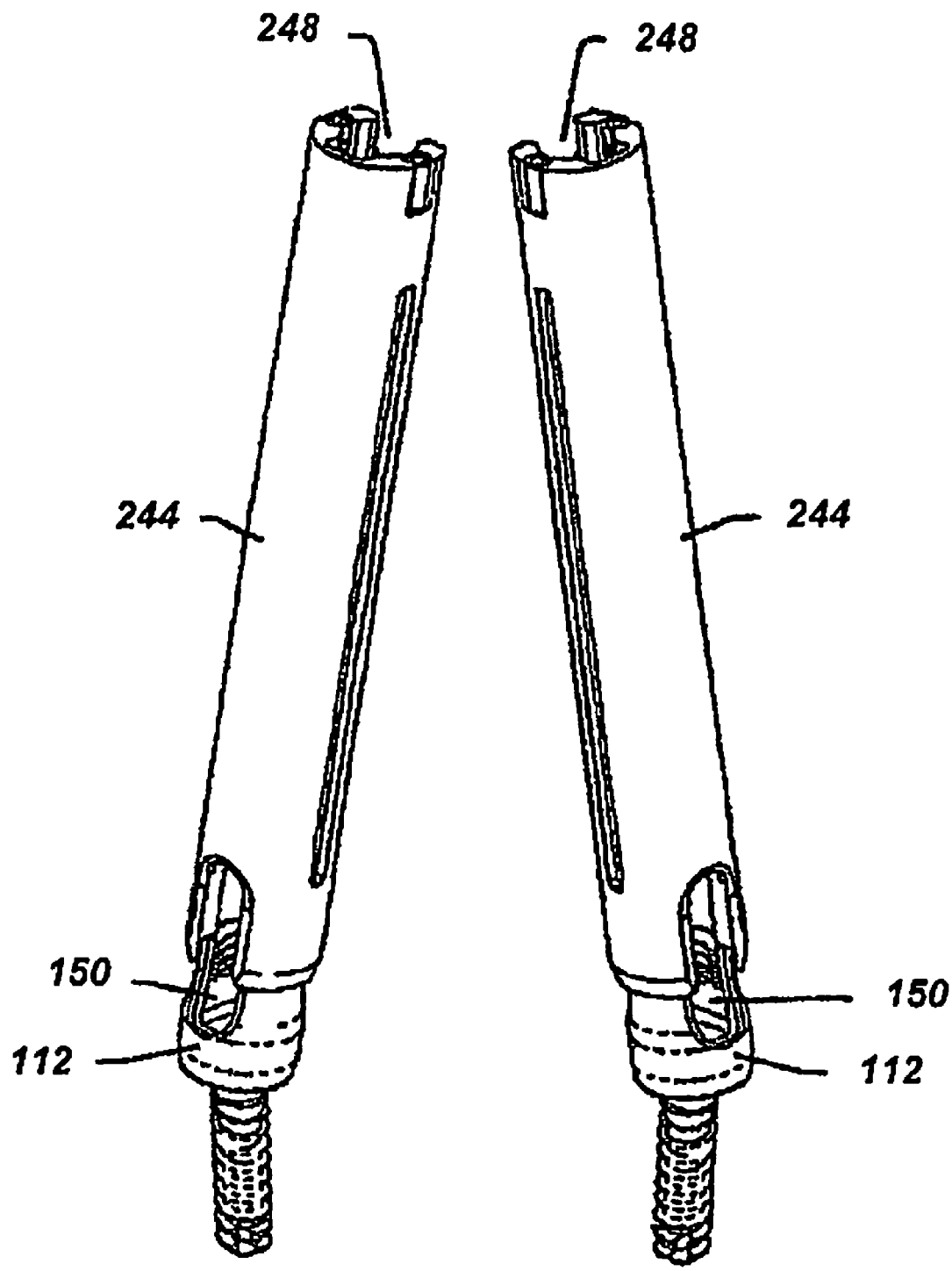
FIG. 29 depicts a perspective view of one embodiment of sleeves that are coupled to bone fastener assemblies.

In some embodiments, channels of detachable members may face a direction other than toward each other. FIG. 29 depicts sleeves 244 coupled to collars 112 oriented at an angle so that channels 248 of sleeves 244 face in different directions. In some embodiments, channels in the detachable member may not be longitudinal channels down the length of the detachable member. In embodiments of detachable members with non-longitudinal channels, the channels of two adjacent detachable members may not face towards each other when the openings of collars coupled to the detachable members are aligned.

Figure 30:
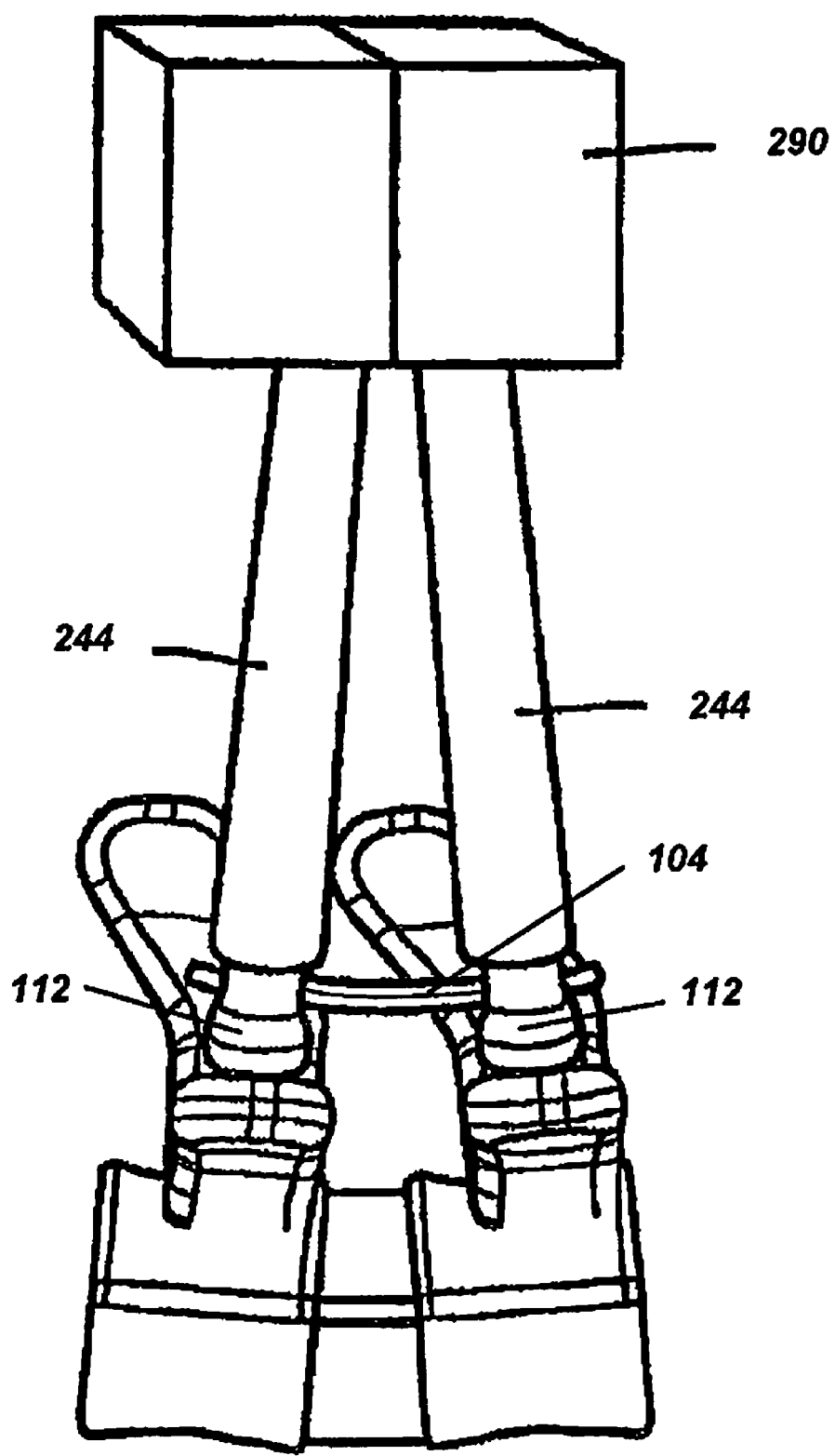
FIG. 30 depicts a schematic view of sleeve embodiments that are coupled to one embodiment of a frame.

In one embodiment, a frame may couple to two or more detachable members. FIG. 30 depicts a perspective view of sleeves 244 coupled to frame 290. FIG. 30 further depicts rod 104 with a non-circular cross-sectional profile spanning between two collars 112. As used herein, a "frame" includes any of a variety of structural elements including, but not limited, rods, bars, cages, or machined blocks. In some embodiments, frame 290 may provide a rigid coupling between sleeves 244. In other embodiments, frame 290 may allow for angular or translational movement between sleeves. For example, frame 290 may include slidable elements that allow sleeves to be translated toward each other or away from each other to facilitate compression or distraction of vertebrae. Alternatively, frame 290 may enable sleeves 244 to pivot toward each other or away from each other. In some embodiments, frame 290 may allow for movement of sleeves 244 to facilitate spinal reduction.

After a bone fastener assembly is coupled to a detachable member, a driver may be coupled to a bone fastener of the bone fastener assembly. The driver may be used to insert the bone fastener into vertebral bone.

Figure 31:
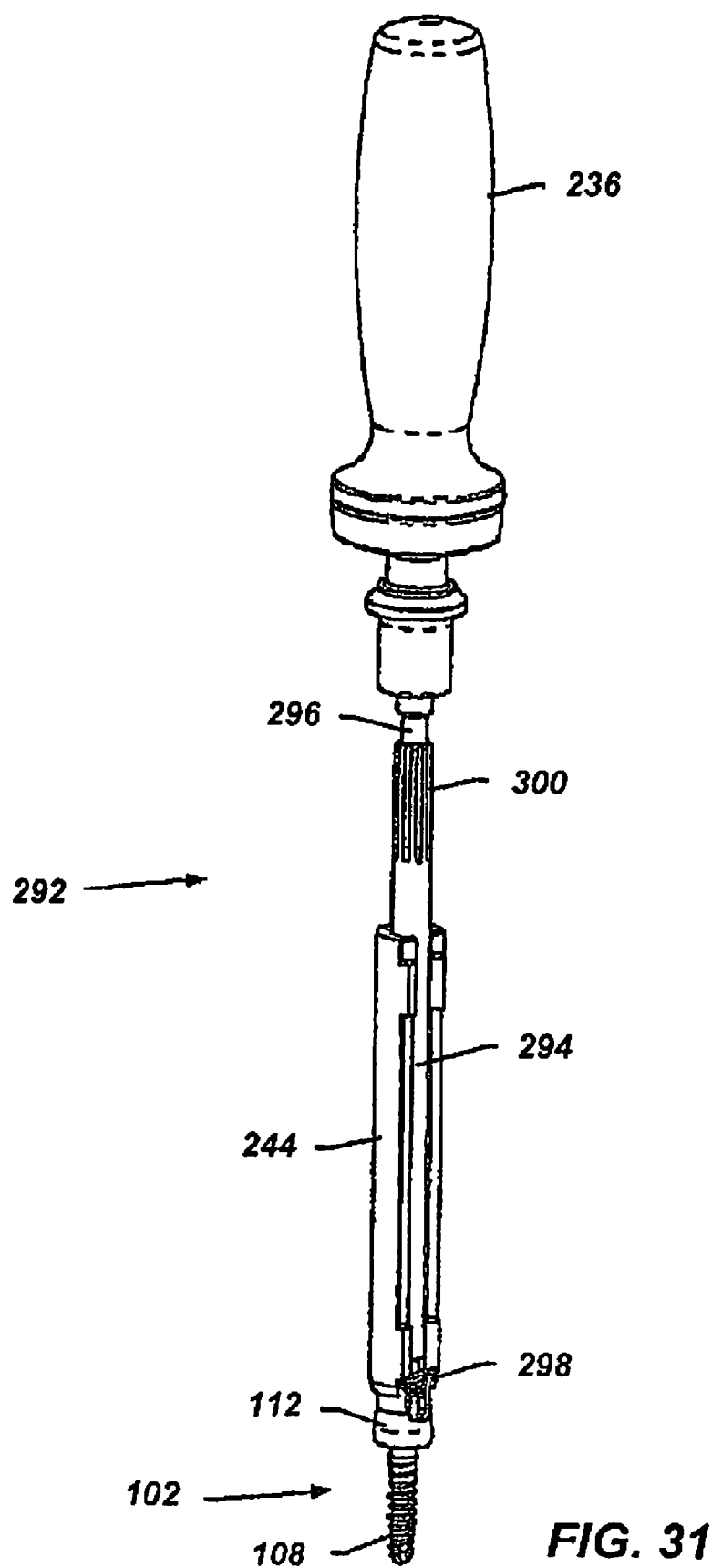
FIG. 31 depicts a perspective view of one embodiment of a driver coupled to a bone fastener and a sleeve.

FIG. 31 depicts one embodiment of driver 292 positioned in sleeve 244. Sleeve 244 is coupled to bone fastener assembly 102. Driver 292 may be coupled to collar 112 and to bone fastener 108 of bone fastener assembly 102. Coupling driver 292 to collar 112 and to bone fastener 108 may ensure proper alignment of the driver relative to the bone fastener. Coupling driver 292 to collar 112 and to bone fastener 108 may also inhibit movement of collar 112 relative to bone fastener 108 during insertion of bone fastener 108.

Driver 292 may include outer shaft 294, inner shaft 296, and removable handle 236. Outer shaft 294 may include threading 298 and textured portion 300. A portion of outer shaft 294 may be positioned in a passage through sleeve 244 (passage 250 shown in FIG. 13). Threading 298 may couple to a modified thread of collar 112. Textured portion 300 may facilitate rotation of outer shaft 294 so that threading 298 engages the modified thread of collar 112. When threading 298 engages the modified thread of collar 112, driver 292 may be securely coupled to bone fastener assembly 102, which is securely fastened to sleeve 244.

A distal end of inner shaft 296 may be coupled to bone fastener 108 during use. Inner shaft 296 may be coupled at a proximal end to removable handle 236 during use. Inner shaft 296 may be rotatable relative to outer shaft 294 so that bone fastener 108 can be inserted into vertebral bone. A proximal portion of inner shaft 296 may include at least one flat portion that fits in a mating portion of removable handle 236. Removable handle 236 may be the same removable handle that is used with bone tap 592 that forms a threaded opening in vertebral bone for a bone fastener 108. Removable handle 236 may be removed from driver 292 during insertion of guide wire 218 through driver 292 so that guide wire 218 may be held in at least one place at all times. In some embodiments, a removable handle for the driver may be unnecessary given the length of guide wire 218 and/or the length of the driver (e.g., a long guide wire 218 and/or a short driver).

Figure 32:
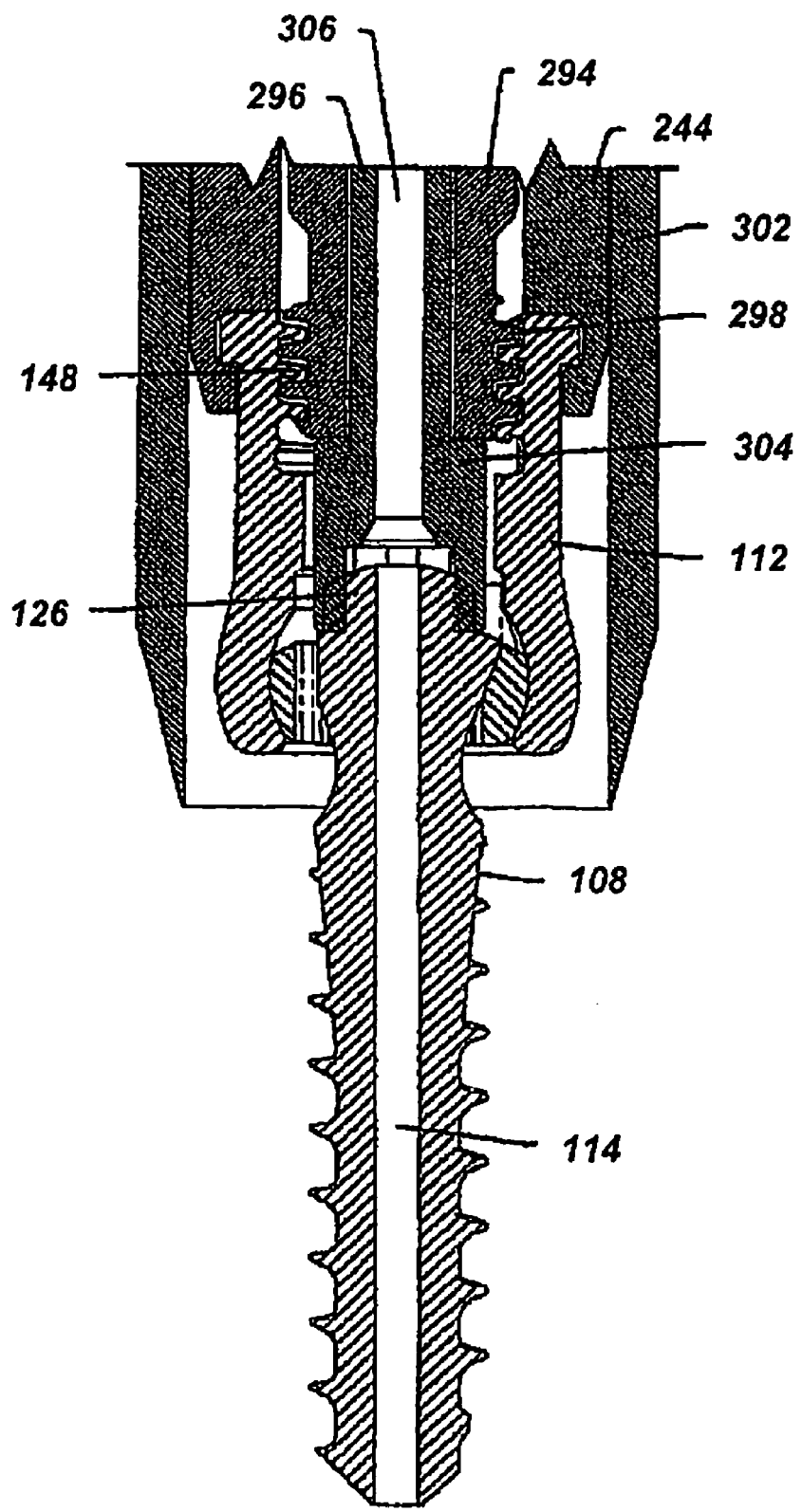
FIG. 32 depicts a partial cross-sectional view of one embodiment of a bone fastener and collar coupled to a driver positioned in a dilator.

FIG. 32 depicts a cross-sectional representation of a portion of one embodiment of a driver that is coupled to bone fastener 108 and collar 112 of a bone fastener assembly. Collar 112 is coupled to sleeve 244. Sleeve 244 is positioned in dilator 302. In some embodiments, clearance between outer shaft 294 and sleeve 244 may be relatively small. In some embodiments, the clearance between outer shaft 294 and sleeve 244 may range from about 0.1 mm to about 0.75 mm. For example, the clearance between outer shaft 294 and sleeve 244 may be about 0.25 mm (i.e., an inner diameter of the sleeve may be about 0.5 mm greater than an outer diameter of the outer shaft). Also, clearance between sleeve 244 and dilator 302 may be relatively small. The small clearances may inhibit undesired movement of the instruments relative to each other and/or reduce bulkiness at the surgical site.

Thread 298 of outer shaft 294 of the driver may couple to modified thread 148 of collar 112. Head 304 of inner shaft 296 of the driver may couple to tool portion 126 of bone fastener 108. Head 304 may have a complementary shape to tool portion 126 of bone fastener 108. Guide wire 218 may be inserted into a distal end of passage 114 of bone fastener 108 and through passage 306 of the driver. When guide wire 218 is inserted into passage 114 and passage 306, a removable handle may not be coupled to inner shaft 296.

In operation, wire 400 can be used to guide components from the exterior of the patient via a first incision or a second incision to bone fastener assembly 102 advanced into the patient via a third insertion such that rod 104 can be guided under tissue and muscle to another sleeve/collar assembly advanced into the patient via a fourth incision. A scalpel may be used to make an incision in the patient. Wire 400 and/or rod 104 can be radiolucent or contain markers that allow placement of wire 400 and rod 104 to be viewed under medical imaging such fluoroscopy.

Figure 33:
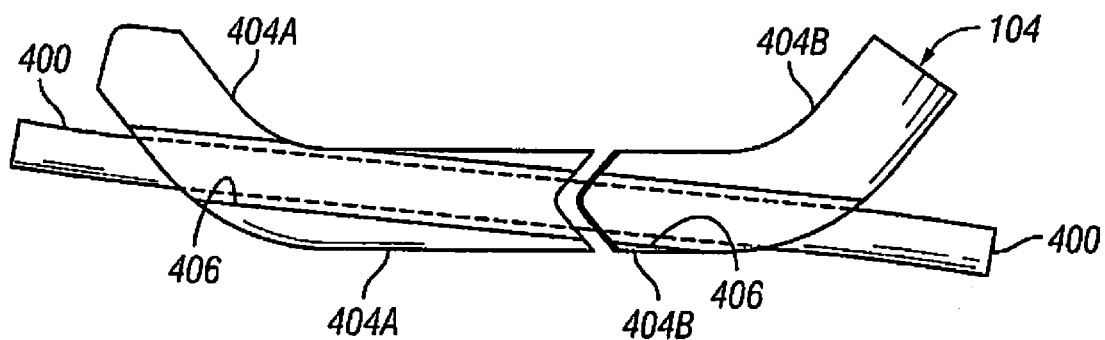
FIG. 33 depicts a side view of one embodiment of a rod having multiple segments.

FIG. 33 depicts a side view of one embodiment of rod 104 comprising segments 404. Segments 404 may connect to other segments 404 using either end, or may have one end for connecting with other segments 404 and a second end shaped to ease passage through or under tissue 460. In some embodiments, rod 104 can include rounded, beveled, tapered or otherwise shaped ends. First segment 404A may have a desired characteristic, such as the curvature along its length as depicted in FIG. 33. In FIG. 33, first segment 404A may be engaged with wire 400 such that a surface aligns with a surface of wire 400. Second segment 404B may have a desired characteristic, such as the curvature along its length depicted in FIG. 33. Second segment 404B may be engaged with wire 400 such that a surface of second segment 404B aligns with a surface of wire 400. When first segment 404A and second segment 404B are connected to form rod 104 and attached to bone fastener assemblies 102, spine stabilization system 100 may have a desired overall curvature. For example, if segments 404A and 404B have the same curvature, indexing second segment 404B 180 degrees enables rod 104 to have a single curvature. Alternatively, if segments 404A and 404B are indexed 180 degrees from each other, rod 104 may have an S-shaped configuration. An advantage to this embodiment is that an instrumentation kit may include relatively few segments, and the surgeon need only index segments 404A, 404B, etc., onto wire 400 to construct rod 104 having a selected curvature. While the characteristic of segments 404A and 404B are described as curvatures with respect to FIG. 33, other characteristics are possible, such as torsional stiffness, tensile strength, compressive strength, hardness, biocompatibility, or the like. As shown in FIG. 33, rod 104 can have passage 406 along a portion thereof such that rod 104 can be advanced along wire 400. In such one embodiment, wire 400 can first be run along insertion path 455 to assemblies 450A and 450B as shown in FIG. 33. Rod 104 can then be placed by guiding rod 104 using wire 400 in passage 406.

Figure 34:
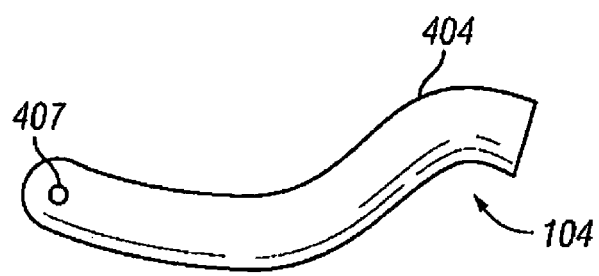
FIG. 34 depicts a side view of one embodiment of a segment of one embodiment of a rod.
Figure 35:
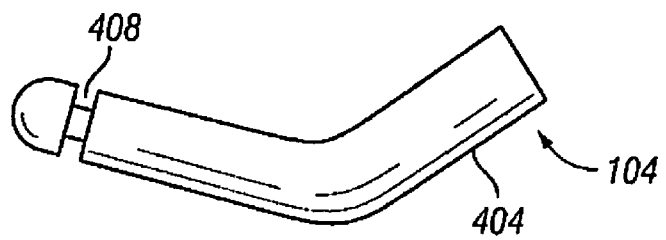
FIG. 35 depicts a side view of one embodiment of a segment of one embodiment of a rod.
Figure 36:
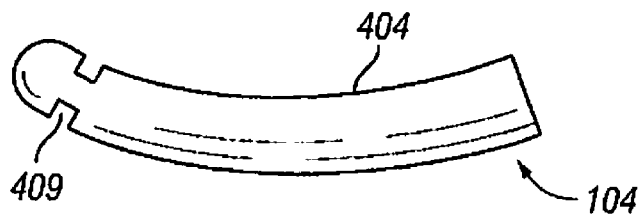
FIG. 36 depicts a side view of one embodiment of a segment of one embodiment of a rod.

FIGS. 34, 35, and 36 depict side views of segments 404 of rod 104, in which an end of segment 404 has a feature such as hole 407, groove 408, or notch 409 for attachment to wire 400 such that rod 104 can be pulled via wire 400. FIG. 34 depicts a side view of one embodiment of segment 404 having opening 407. FIG. 34 further depicts segment 404 having two curves. FIG. 35 depicts a side view of one embodiment of segment 404 having groove 408 extending about segment 404. FIG. 35 further depicts segment 404 having an angle. FIG. 36 depicts a side view of segment 404 having notch 409. FIG. 36 further depicts segment 404 having a bend. Those skilled in the art will appreciate that there are other methods for using wire 400 to advance rod 104 or segments 404. In some embodiments, a bead or knot located on wire 400 may be larger than passage 406 in segment 404 such that tensioning wire 400 contacts a bead or knot with segment 404 and further tensioning pulls segment 404 with wire 400.

Figure 37:
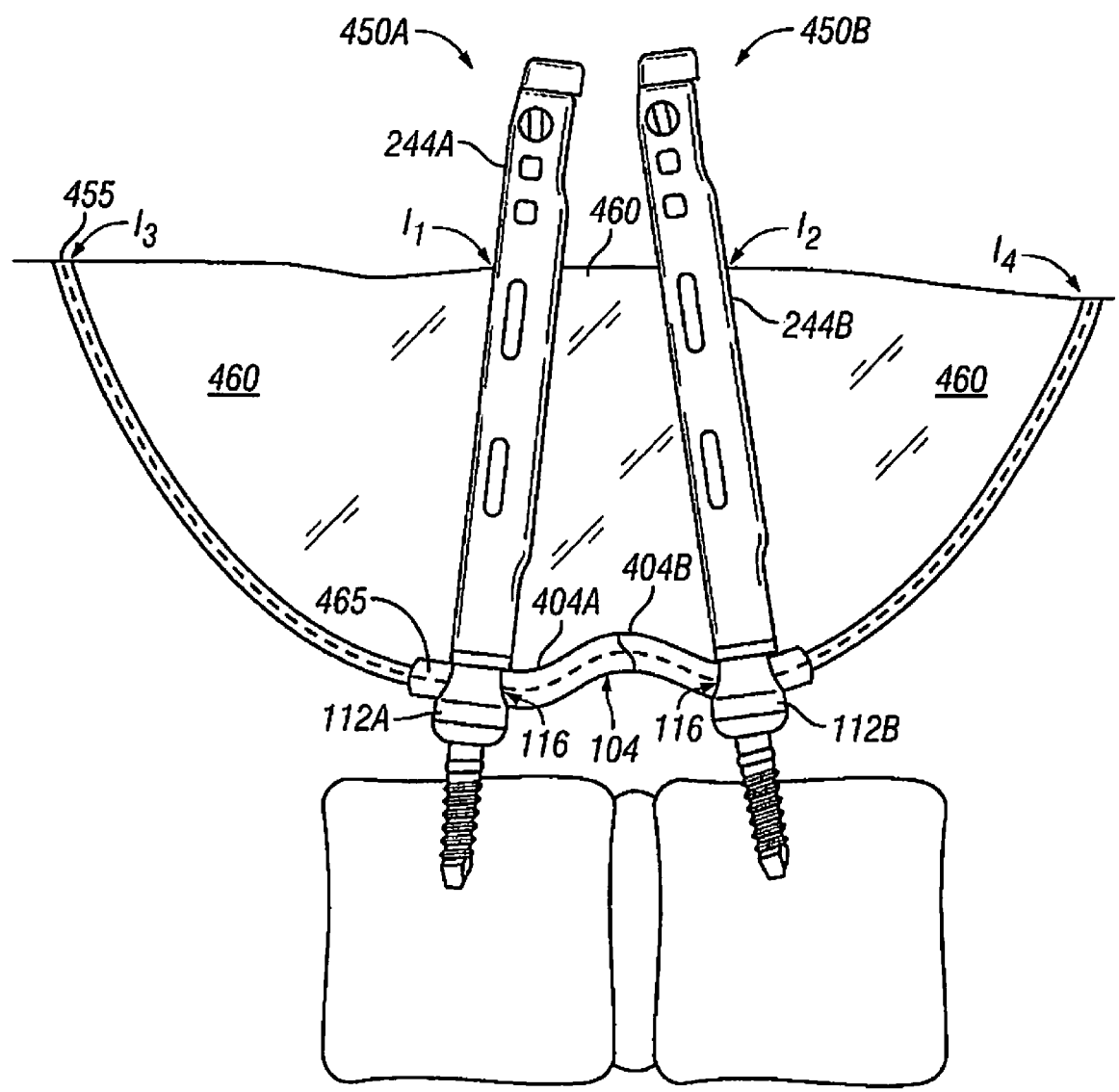
FIG. 37 depicts a side view of one embodiment of a spine stabilization system illustrating a method for advancing a rod into one embodiment of a bone fastener assembly.
Figure 38:
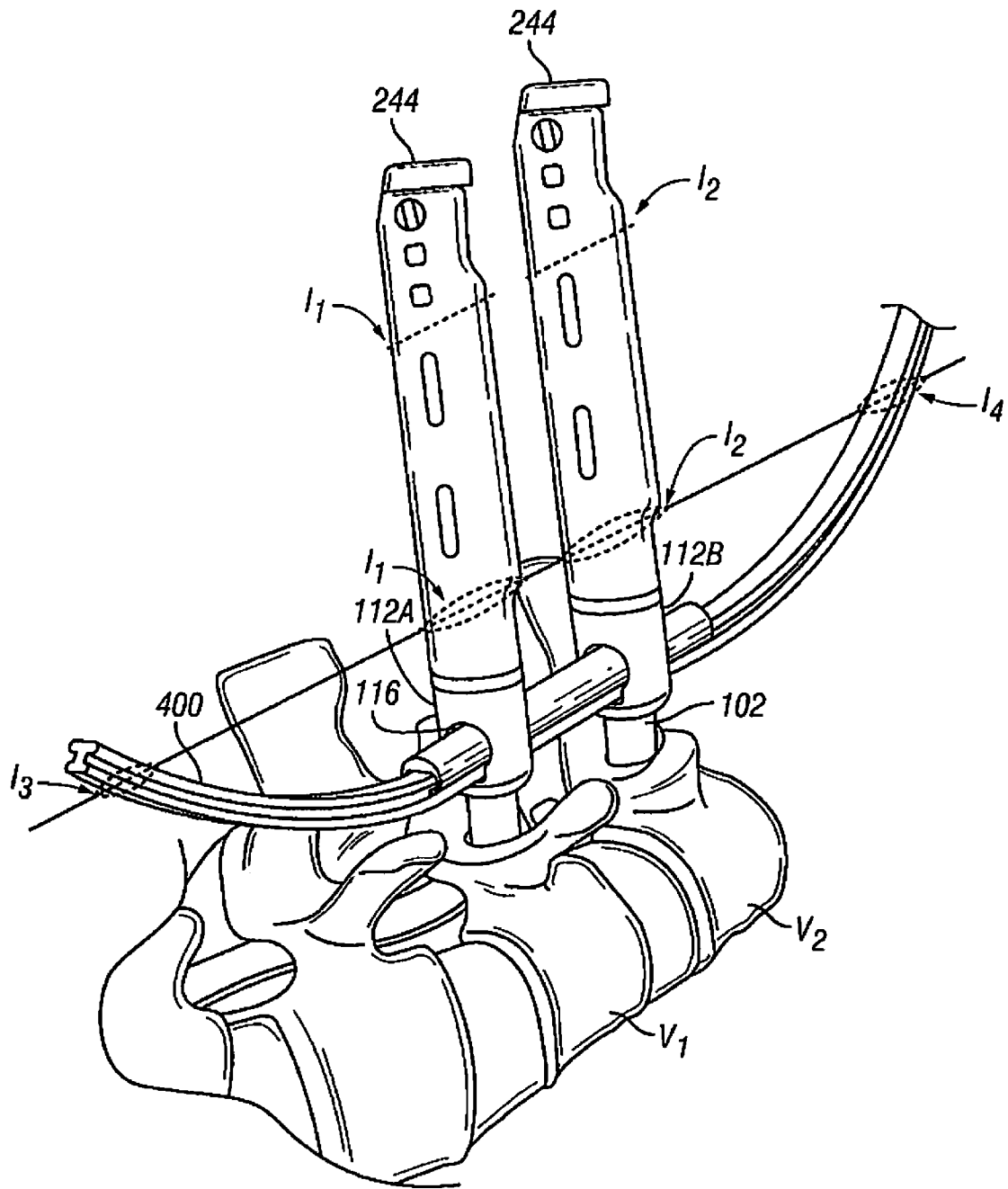
FIG. 38 depicts a perspective view of one embodiment of a spine stabilization system illustrating a method for advancing a rod into one embodiment of a bone fastener assembly.

FIGS. 37 and 38 illustrate embodiments for placement of rod 104 using wire 400 and assemblies 450A and 450B. Various surgical tools can be used to position and move rod 104 along wire 400. Referring to FIG. 37, sleeve 244A can be advanced through a first incision $I_1$ in tissue 460 and coupled to collar 112A to form assembly 450A, and sleeve 244B can be advanced through a second incision $I_2$ in tissue 460 and coupled to collar 112B to form assembly 450B. When sleeve 244A is in place, wire 400 can be inserted into a third incision $I_3$ in tissue 460. As wire 400 moves, it can displace tissue and muscle to define path 455. Wire 400 may be advanced through openings 116 (not visible in FIG. 37) in collar 112A and collar 112B, and advanced until wire 400 exits the patient via a fourth incision $I_4$ in tissue 460. First segment 404 of rod 104 can be engaged to wire 400 so that a first portion of first segment 404 enters the patient through the third incision $I_3$, advances along a path defined by wire 400, passes through a first side of assembly 450A, out the obverse side of assembly 450A, passes through a first side of assembly 450B, and may pass out the obverse side of assembly 450B. As shown in FIGS. 37 and 38, wire 400 may pass through openings 116 in collar 112A and 112B and rod 104 (or segments 404) can pass through openings 116 in collar 112A (shown in FIG. 37) and pass through openings 116 in collar 112B. Segments 404 may be connected to form rod 104. Rod 104 can be oriented by rotating wire 400. Rod may be secured to bone fastener assemblies 102, forming spine stabilization system 100 individually suited for the patient. Sleeves 244 may be uncoupled from collars 112 and removed. Wire 400 may be withdrawn from the third incision $I_3$ or advanced through the fourth incision $I_4$. Alternatively, wire 400 may be cut or severed by a tool such that a portion of wire 400 remains in the body. In one embodiment, leaving a portion of wire 400 inside rod 104 may provide additional support for the spine.

After rod 104 has been positioned in collars 112 as desired, closure members may be used to secure rod 104 to collars 112. FIGS. 39A and 39B depict perspective views of driver 354. Driver 354 may be used to position a closure member in a collar of a bone fastener assembly.

FIG. 40A depicts driver 354 with coupled closure member 106 positioned for insertion in sleeve 244 to couple rod 104 having a non-circular cross-sectional profile to collars 112.

After insertion of driver 354 in sleeve 244, closure member 106 may be positioned proximate collar 112. With driver 354 positioned in sleeve 244, as shown in FIG. 40B, the driver may be rotated to advance closure member 106 in collar 112 and secure rod 104 to collar 112. When closure member 106 is snug and rod 104 is secured, driver 354 may be disengaged from closure member 106 and removed from sleeve 244. In one embodiment, driver 354 may be used to secured closure member 106. In certain embodiments, driver 354 may include a mechanism to dislodge a closure member and/or a tool portion of a closure member from the distal end of the driver.

Figure 41:
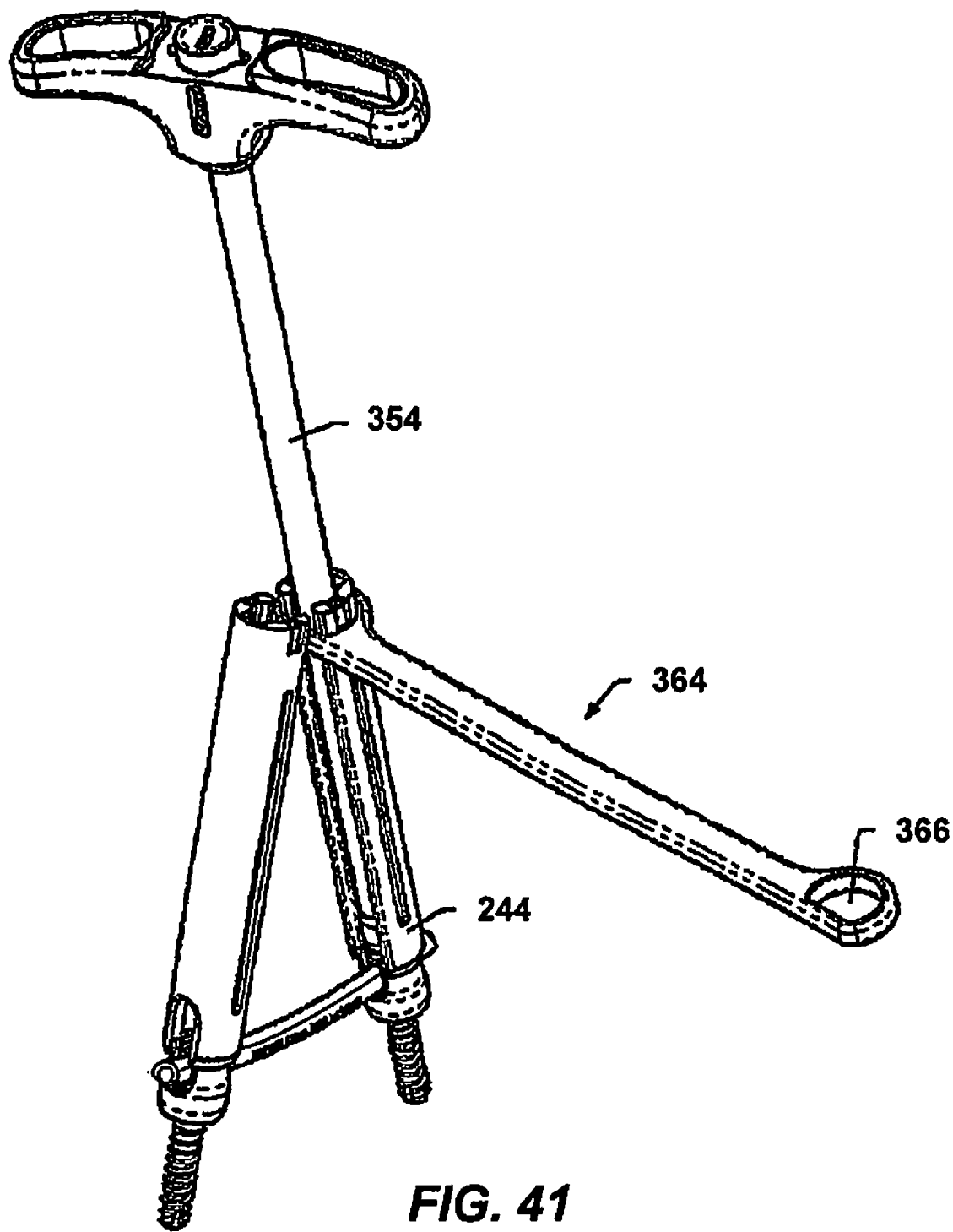
FIG. 41 depicts one embodiment of a counter torque wrench coupled to a sleeve.

In some embodiments, a detachable member may be held with a counter torque wrench as the tool portion of a closure member is secured. In one embodiment, about 120 in-lbs of torque may be required to secure a closure member. A counter torque wrench may inhibit transfer of force to the patient when a closure member is being secured to a collar. FIG. 41 depicts one embodiment of counter torque wrench 364 used to inhibit application of torque to a patient's spine during a closure member. Sleeve 244 may fit in opening 366 of counter torque wrench 364. Counter torque wrench 364 may be positioned near a proximal end of sleeve 244 during use. Force may be applied to counter torque wrench 364 in a direction opposite to rotational force applied to driver 354 to secure closure member 106. Opening 366 in torque wrench 364 may be of any shape to accommodate a cross-sectional shape of sleeve 244 and inhibit rotation of the sleeve during use.

Figure 43:
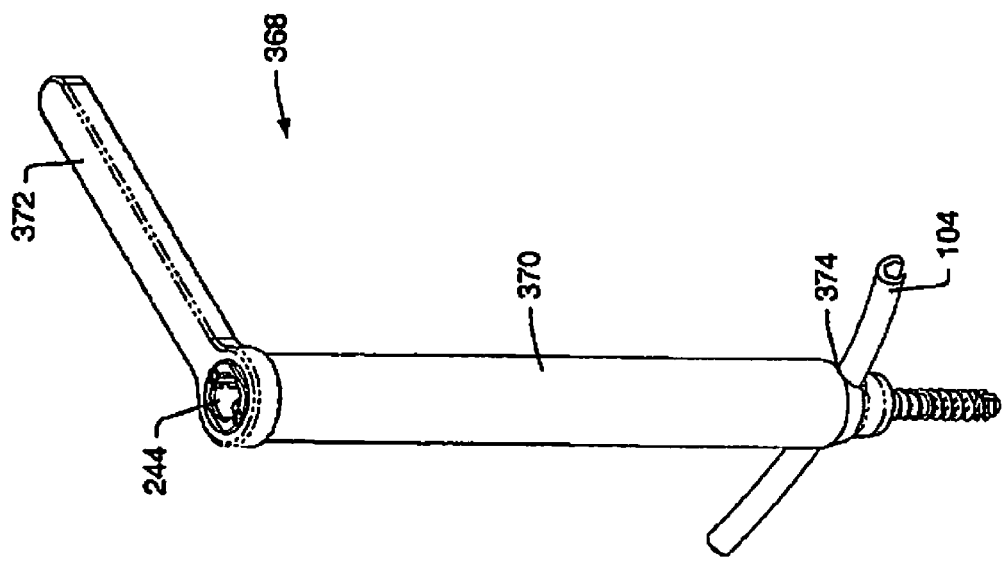
FIG. 43 depicts a schematic view of the counter torque wrench shown in FIG. 42 coupled to a rod.
Figure 42:
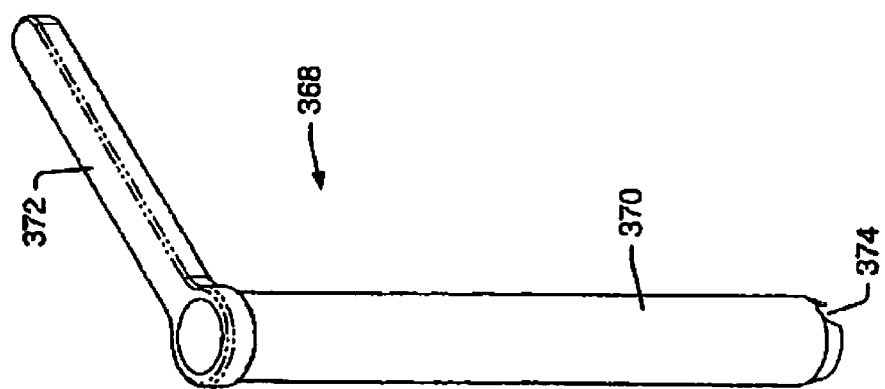
FIG. 42 depicts one embodiment of a counter torque wrench.

FIG. 42 depicts one embodiment of counter torque wrench 368 designed to accommodate sleeves. Counter torque wrench 368 may include hollow shaft 370 and handle 372. Groove 374 may be located at a distal end of hollow shaft 370. FIG. 43 depicts counter torque wrench 368 fitted over multi-channel sleeve 244. In one embodiment, hollow shaft 370 may be inserted through an opening in the body over sleeve 244 and advanced toward the spine until rod 104 is seated in groove 374. Counter torque wrench 368 may engage the spine stabilization system. Force may be applied to counter torque wrench 368 in a direction opposite to rotational force applied to a driver used to secure closure member 106. During a minimally invasive spine stabilization procedure, counter torque wrench 368 may be used with various types of detachable members, including single-channel sleeves and multi-channel sleeves.

Minimally invasive procedures may involve locating a surgical site and positions for four skin incisions to access the surgical sites. First and second incisions may be located above vertebrae to be stabilized. Third and fourth incisions may be located along the spine some distance from the first and second incisions. An opening in the tissue under the skin may be enlarged to exceed the size of the skin incisions. Movement and/or stretching of an incision and angulation of collars of bone fastener assemblies may allow the length of the incision to be minimized. In some embodiments, minimally invasive insertion of a spine stabilization system may not be visualized. In certain embodiments, insertion of a spine stabilization system may be a top-loading, mini-opening, muscle-splitting, screw fixation technique.

In one embodiment of a spine stabilization system insertion method, the patient may be placed in a prone position on a radiolucent table with clearance available for a C-arm of a fluoroscope. For example, a Jackson table with a radiolucent Wilson frame attachment may be used. The ability to obtain high quality images is very important. Bolsters, frames, and pads may be inspected for radiolucency prior to the operation. Placing the patient in a knee-chest position (e.g., using an Andrews table) should be avoided. Care should be taken to avoid placing the patient's spine in kyphosis during positioning of the patient.

The C-arm of the fluoroscope should be able to freely rotate between the anteroposterior, lateral, and oblique positions for optimal visualization of pedicle anatomy during the procedure. The arm should be rotated through a full range of motion prior to beginning the procedure to ensure that there is no obstruction or radio-opaque object in the way. The fluoroscope may be positioned so that Ferguson views and "bullseye" views are obtainable. Once the patient is positioned and the ability to obtain fluoroscopic images of the target levels for instrumentation has been confirmed, the patient may be prepared and draped sterilely.

For most of the lumbar region, the vertebral pedicle is an obliquely oriented cylindrical corridor. The angulation varies by approximately 5 degrees per level (e.g., L1: 5 degrees; L5: 25 degrees). A pre-operative fine-cut computed tomography image may be examined to determine any unique anatomy of the patient. Acquiring the pedicle in the most lateral and superior quadrant of the pedicle may be desirable to avoid the overriding facet during a minimally invasive procedure. A lateral entry point may allow for better screw convergence as well as less interference with the superior adjacent level facet joint. A targeting needle may be passed in a medial and inferior trajectory, thus following the natural pathway of the pedicle. Frequent fluoroscopic inspection in both an anteroposterior and lateral plane may ensure proper passage of the needle as the needle is inserted into vertebral bone.

Various techniques may be used to plan the skin incisions and entry points. In one embodiment, the planning sequence for single-level stabilization may include the following four steps. First, an anteroposterior image may be obtained with the spinous processes centered at the target vertebral bodies. Vertical lines passing through midpoints of pedicles that are to receive bone fasteners may be marked on the patient. The lines do not represent skin entry points. The lines are markers of pedicle entry points used to estimate angles at which targeting needles to be inserted to contact the pedicles. In some embodiments, sets of vertical lines may be drawn corresponding to the lateral edges of the pedicles instead of lines corresponding to the midpoints of the pedicles.

Second, horizontal lines may be marked approximately through the centers of the pedicles (mid-pedicle lines) on the patient. In some embodiments, the lines may be drawn on the superior side of the center axes (superior to the mid-pedicle).

Third, an oblique or "bullseye" view (i.e., down a longitudinal axis of a pedicle) may be obtained on each side of the patient for each pedicle that is to be stabilized. Vertical oblique view lines may be marked on the skin at the midpoints of each of the pedicles that are to receive a bone fastener. The oblique view lines may be drawn in a different color than the vertical lines drawn during the first step. In some embodiments, vertical lines may be drawn corresponding to the lateral edges of the pedicles instead of lines corresponding to the midpoints of the pedicles.

The oblique view lines may be about 2 cm to about 3 cm away from the lateral pedicle border lines marked in the first step. For larger patients, the oblique view line may be greater than about 3 cm away from the midline marked in the first step. For smaller patients, the oblique view line may be closer than about 2 cm away from the midline marked in the first step. The intersection of the oblique view lines with the horizontal lines drawn in the second step may represent skin entry points for a targeting needle as the targeting needle passes through soft tissue at an angle towards the bony pedicle entry point. A side fluoroscopic image, the horizontal lines, and the vertical lines may help the surgeon triangulate between the skin entry points and bony entry points.

Fourth, an incision may be made in the skin between mid-pedicle lines along the vertical oblique view lines. The skin incision may be from about 2 cm to about 4 cm long. In some embodiments, the incision may be from about 2.5 cm to about 3 cm long. Limiting the length of the incision may enhance patient satisfaction with the procedure. The incisions may be pre-anesthetized with, for example, 1% lidocaine with 1:200,000 epinephrine. To blunt the pain response, a long spinal needle may be used to dock on the bone entry point and inject the planned muscle path in a retrograde fashion as well. Once the incision has been made, tissue surrounding the incision may be pulled and/or stretched to allow access to a target location in a vertebra.

After sterile preparation and draping, the pedicle entry points may be fluoroscopically rechecked to ensure that the previously marked lines correspond to the intersection of the midline of the transverse process and the lateral joint and pars interarticularis. The intersection of the facet and the transverse process provides a starting point that may help avoid the canal and follow the natural inclination of lumbar pedicles. For the spine stabilization system described, in which sleeves coupled to bone fastener assemblies are substantially unconstrained by insertion angles of the bone fasteners, patient anatomy may determine the most advantageous insertion angles of the bone fasteners.

A scalpel may be used to make a stab wound at the junction of an oblique view line and a mid-pedicle line. In one embodiment, the scalpel may be a #11 scalpel. A targeting needle may be passed through the incision in an oblique lateral to medial trajectory towards the bony entry point defined by a lateral pedicle border line. The C-arm of the fluoroscope may be placed in an anteroposterior position for this maneuver.

Insertion of a spine stabilization system may include gradually increasing the diameter of an opening formed in a pedicle and/or vertebral body to accept a bone fastener assembly. For example, a targeting needle may have outer diameter of about D. A bone awl inserted after the targeting needle may have an outer diameter incrementally larger than the outer diameter of the targeting needle. As used herein, an incrementally larger diameter may be large enough to allow a snug but adjustable fit. For example, the bone awl may have outer diameter of about (D+x). A tap portion of a bone tap inserted after the bone awl may have a minor diameter of about (D+2x). A bone fastener may have a minor diameter of about (D+3x). In some embodiments, x may be between about 0.1 mm and about 1.0 mm. For example, x may be about 0.5 mm. Incremental sizing of the targeting needle, bone awl, tap, and bone fastener may promote a proper fit of the bone fastener in the vertebra to be stabilized.

As the targeting needle encounters the bony anatomy, anteroposterior fluoroscopic images may be used to place the tip of the needle at the upper outer quadrant of the pedicle. In some embodiments, the needle may be walked medially along the transverse process to the pedicle entry point. In some embodiments, the needle tip may be docked by lightly tapping the tip into the bone with a mallet or other impact device to drive the tip into the bone. In some embodiments, the needle tip may be docked by applying downward pressure to the targeting needle to force the tip into the bone.

The fluoroscope may then be moved to a lateral position. The surgeon may correct the sagittal trajectory of the needle by moving the needle in an anterior or posterior direction to match the vector of the pedicle corridor. In some embodiments, a mallet or other impact device may be used to gently advance the targeting needle into the pedicle halfway to the pedicle-vertebral body junction. In other embodiments, force may be applied to the targeting needle to drive the targeting needle into the pedicle halfway to the pedicle-vertebral body junction. An anteroposterior image may then be obtained to confirm that the needle is approximately halfway across the pedicle in the anteroposterior view. If the tip is more than halfway across the pedicle in a lateral to medial projection, the trajectory may be too medial. Further advancement of the needle may risk passing the needle through the spinal canal. The needle may be repositioned. A new starting point or new trajectory may be obtained. If the anteroposterior image demonstrates that the needle is significantly lateral in the pedicle, then the needle may have passed along the lateral portion of the pedicle. A needle that has passed along the lateral portion of the pedicle may be withdrawn and repositioned.

Once a good trajectory has been obtained, the targeting needle may be advanced using a mallet. In some embodiments, the needle may be pushed in without a mallet. The targeting needle may be advanced to the junction of the pedicle and vertebral body under lateral fluoroscopic guidance. FIG. 44A depicts targeting needle 198 advanced to the junction of pedicle 164. At this point, confirmation of position and trajectory should be repeated under anteroposterior fluoroscopy. Targeting needle 198 may be further advanced to a desired depth within vertebral body 166 using a mallet or applied force. FIG. 44B depicts targeting needle 198 advanced to the desired depth.

A scale on targeting needle 198 may be used to approximate a length of a bone fastener to be used. A first depth of targeting needle 198 may be measured relative to body surface 376 when pedicle 164 is first encountered. A second depth of targeting needle 198 may be measured relative to body surface 376 after the targeting needle has been advanced to the desired depth in vertebral body 166. An approximate length of the pedicle screw to be used may be determined by taking a difference between the depth measurements.

After targeting needle 198 has been advanced into the bone, member 202 of the targeting needle (shown in FIG. 44B) may be removed from the targeting needle. FIG. 44C depicts outer housing 200 with the member removed. After removal of the member, guide wire 218 may be placed through a passage in targeting needle 198 into vertebral body 166. FIG. 44D depicts targeting needle 198 with guide wire 218 positioned through the passage in the targeting needle. Lateral fluoroscopic images may be obtained to indicate the position of guide wire 218. In some embodiments, guide wire 218 may be pushed into vertebral body 166. In certain embodiments, guide wire 218 may be advanced about 1 cm beyond an end of outer housing 200 to secure the guide wire in vertebral body 166. In some embodiments, a small diameter tissue dilator may be placed over guide wire 218 and positioned on an upper surface of the targeting needle. The tissue dilator may provide stability to guide wire 218. Added stability from the dilator may allow guide wire 218 to be successfully tapped into the vertebral body with a small mallet. Care should be taken to avoid kinking guide wire 218. After guide wire 218 is secured in vertebral body 166, outer housing 200 may be removed from the patient. FIG. 44E depicts guide wire 218 after removal of the targeting needle.

Once guide wire 218 has been passed through the targeting needle and the targeting needle has been removed, guide wire 218 may be used as a guide to position one or more successively sized dilators around a target location in a pedicle. A dilator may be a conduit with a regular shape (e.g., cylindrical) or an irregular shape (e.g., C-shaped). A dilator may form an opening through soft tissue to the pedicle. For patients with a thick fascia, it may be advantageous to make a nick in the fascia with a scalpel blade to facilitate passage of the dilators. The dilators may be passed sequentially over guide wire 218. The dilators may be rotated during insertion to facilitate dilation of surrounding tissue. The dilators may be inserted until the leading edges contact the pedicle. A distal end of a dilator may be tapered to facilitate positioning of the dilator proximate the pedicle. An instrumentation set for a spine stabilization system may include two, three, four, or more successively sized dilators.

Figure 45D:
FIGS. 45A-45D depict schematic views of tissue dilation during a minimally invasive spine stabilization procedure.
Figure 45C:
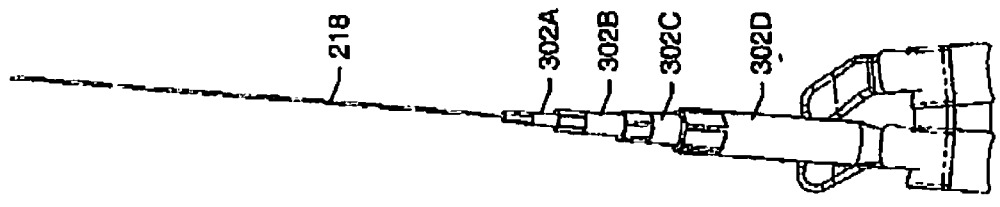
Figure 45B:
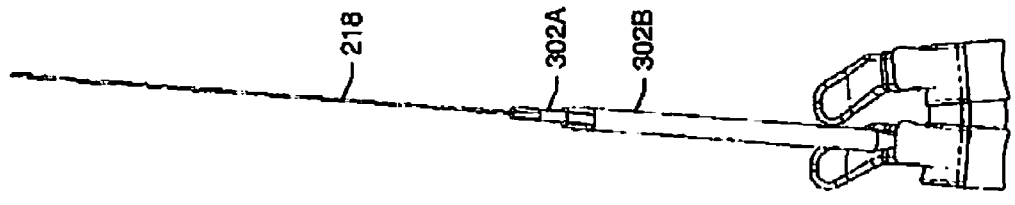
Figure 45A:
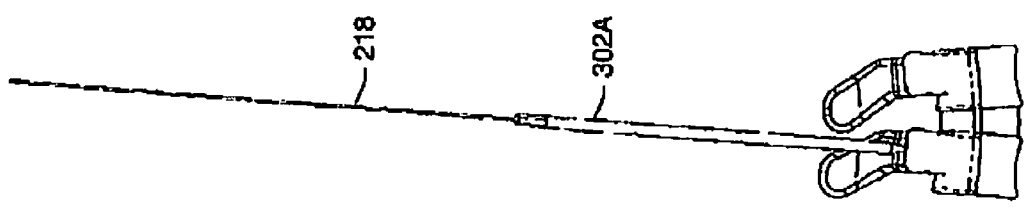

FIG. 45A depicts first dilator 302A positioned around guide wire 218. First dilator 302A may have an inner diameter just slightly larger than an outer diameter of guide wire 218. As used herein, "an inner diameter just slightly larger than an outer diameter" may mean that the inner diameter is between about 0.03 mm and about 1.0 mm greater than the outer diameter. For example, an inner diameter of first dilator 302A may be about 0.5 mm greater than the outer diameter of guide wire 218.

FIG. 45B depicts second dilator 302B positioned around first dilator 302A. Second dilator 302B may have an inner diameter just slightly larger than an outer diameter of first dilator 302A.

FIG. 45C depicts third dilator 302C and fourth dilator 302D and positioned around second dilator 302B. Third dilator 302C may have an inner diameter just slightly larger than an outer diameter of second dilator 302B. Fourth dilator 302D may have an inner diameter slightly larger than an outer diameter of third dilator 302C. Once fourth dilator 302D is in position, dilators 302A, 302B, 302C may be removed, starting with dilator 302A. Lengths of dilators in a successively sized set may decrease with increasing diameter to facilitate removal of the smaller dilators. Care should be taken to avoid dislodging guide wire 218 during insertion and removal of the dilators. FIG. 45D depicts fourth dilator 302D positioned around guide wire 218 following removal of dilators 302A, 302B, 302C.

Figure 46A:
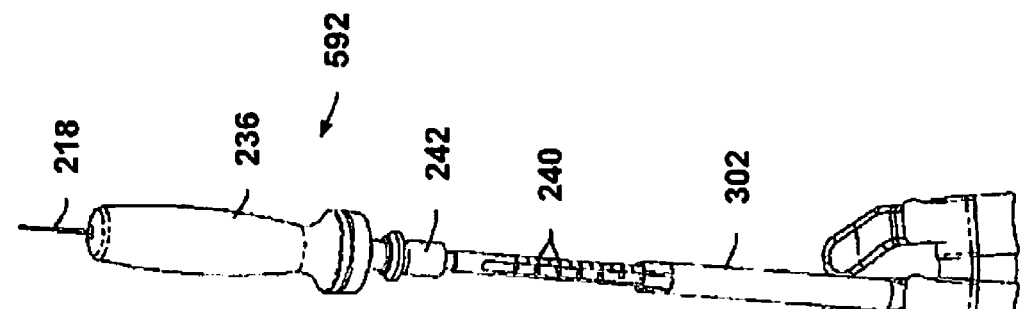
FIGS. 46A-46F depict schematic views of vertebra preparation for receiving a bone fastener assembly during a minimally invasive spine stabilization procedure.
Figure 46B:
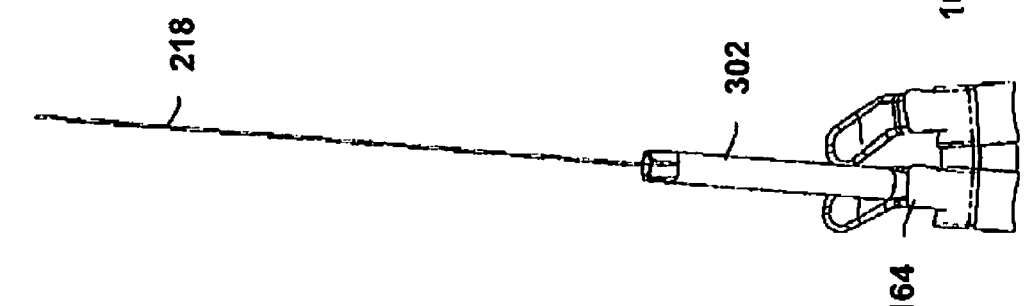
Figure 46C:
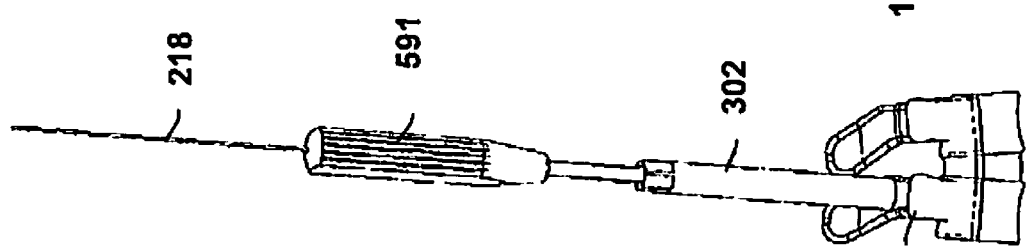

After tissue dilation has been achieved, a large diameter dilator (e.g., third dilator 302C or fourth dilator 302D shown in FIG. 45C) may be used to guide a bone fastener assembly and/or insertion instruments toward a target location in a pedicle. FIGS. 46A-46F depict portions of a procedure for preparation of pedicle 164 and vertebral body 166 for receiving a bone fastener assembly. FIG. 46A depicts bone awl 591 positioned over guide wire 218 in dilator 302 such that a tip of the bone awl is on or near a surface of pedicle 164. Bone awl 591 may be driven downwards into pedicle 164 to breach cortical bone of the pedicle. FIG. 46B depicts a position of bone awl 591 after pedicle 164 has been breached. After pedicle 164 is breached, bone awl 591 may be removed from dilator 302. FIG. 46C depicts guide wire 218 and dilator 302 after removal of bone awl 591. In some embodiments, an initial passage may be formed in the pedicle and the vertebral body using a drill or a drill and tap combination.

Figure 46D:
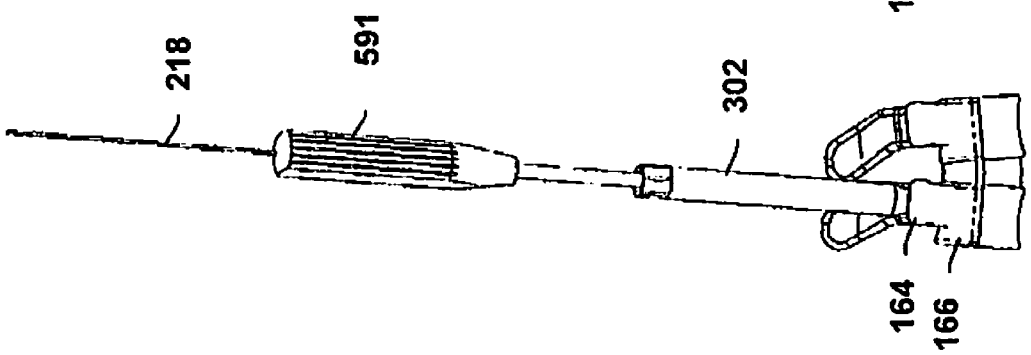

FIG. 46D depicts tap 592 positioned in dilator 302. After pedicle 164 is breached, tap 592 may be inserted over guide wire 218 into dilator 302. In one embodiment, dilator 302 may be third dilator 302C. Tap 592 may be sized to fit snugly inside third dilator 302C. In some embodiments, dilator 302 may be fourth dilator 302D. In certain embodiments, fourth dilator 302D may be inserted over third dilator 302C after bone has been tapped through the third dilator. Tapping through third dilator 302C rather than fourth dilator 302D may introduce less bulk at the target site of a pedicle during the tapping procedure. In some embodiments, an outer diameter of a sleeve coupled to a bone fastener assembly to be inserted in the pedicle may be substantially the same as an outer diameter of third dilator 302C.

Tap 592 may include removable handle 236 and indicia 240. Indicia 240 may be a scale. When tap 592 is positioned such that a first thread flight contacts pedicle 164, a first measurement of the position of the tap relative to a top of dilator 302 using indicia 240 may be noted. Tap 592 may be rotated to form a threaded passage through pedicle 164 and into vertebral body 166 to a desired depth. In some embodiments, a length of the threaded portion of tap 592 may be used to determine a depth of a threaded passage formed in a bone. For a threaded portion of a known length (e.g., 30 mm, 45 mm, 60 mm), a scaled image (e.g., X-ray image) of a depth of the threaded portion in a bone monitored during tapping may allow a medical practitioner to determine the depth of the threaded passage. In some embodiments, tap 592 may form threads of major diameter about 0.5 mm smaller than a major diameter of threads of a bone fastener to be inserted into the threaded passage.

Figure 46E:
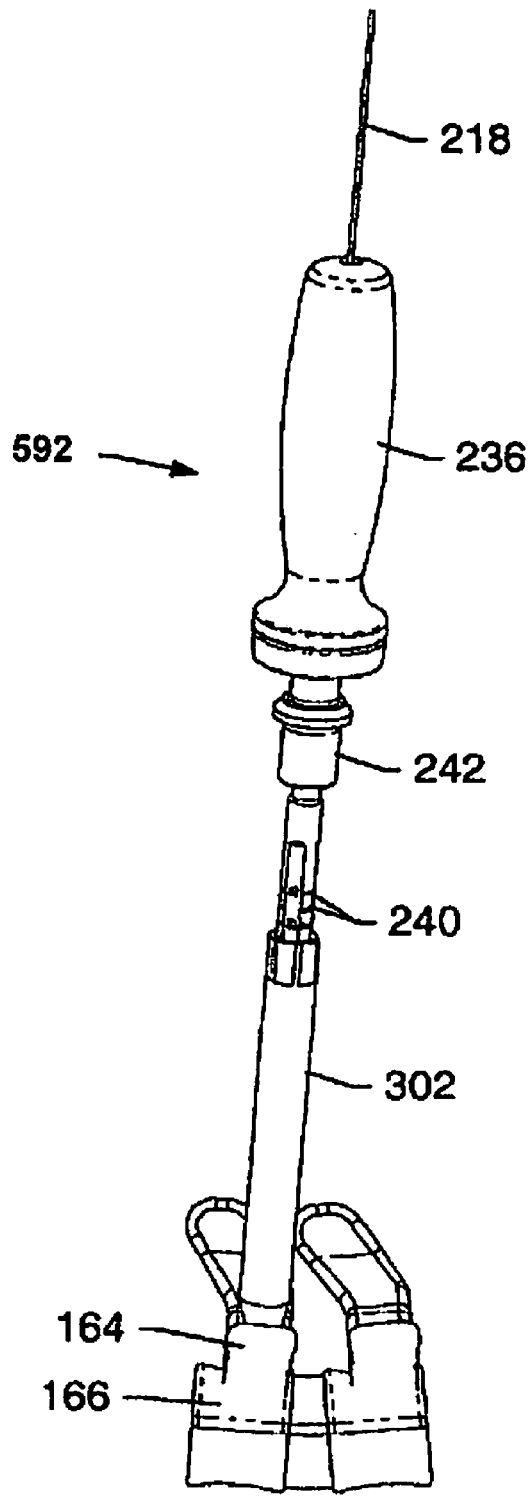

FIG. 46E depicts a position of tap 592 after a threaded passage of a desired length has been formed in pedicle 164 and vertebral body 166. Care should be exercised to ensure that guide wire 218 is not bent or kinked during the tapping process. The position of tap 592 relative to the end of guide wire 218 may be monitored to ensure that guide wire 218 is not dislodged or removed from the vertebra. In some embodiments, a position of tap 592 may be monitored using fluoroscopic imaging.

Figure 46F:
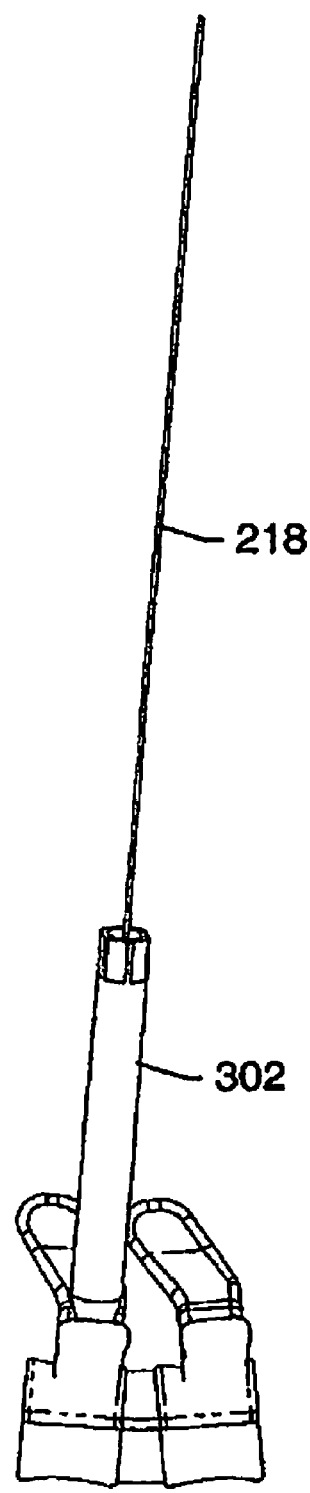

After a threaded passage of a desired length has been formed in pedicle 164 and vertebral body 166, a second measurement of the position of tap 592 relative to a top of dilator 302 using indicia 240 may be noted. A length of a threaded member may be determined by taking a difference between the first and second measurements. In some embodiments, an estimate of length may be derived based upon fluoroscopic images and a known length of the tap that is visibly recognizable in the fluoroscopic images. Tap 592 may be removed from vertebral body 166 and pedicle 164 by rotating the tap out of the vertebral body and the pedicle. Handle 236 may be removed from a blade portion of tap 592. The blade portion of tap 592 may be removed from guide wire 218 with control of guide wire 218 initially maintained from above the tap and then from below the tap. Care may be taken when tap 592 is removed to maintain guide wire 218 in position and to avoid damage of guide wire 218. FIG. 46F depicts dilator 302 and guide wire 218 after removal of the tap.

A bone fastener assembly with a bone fastener of an appropriate length may be selected for insertion in a patient. The size of the bone fastener may be verified with measurement indicia in an instrumentation set. In some embodiments, measurement indicia may be etched or printed on a portion of an instrumentation set. For example, the chosen bone fastener embodiment may be placed over the outline of a bone fastener embodiment printed on a tray of the instrumentation set.

The chosen bone fastener assembly may be attached to a detachable member. In one embodiment, a bone fastener assembly may be rotated on a flange of a detachable member. Movable members of the detachable member may be extended into indentations in a collar of the bone fastener assembly. A driver may be used to extend the movable members to couple with the collar. When the bone fastener assembly is coupled to the detachable member, a drive portion of a fastener driver may be coupled to a tool portion of the bone fastener. A shaft of the fastener driver may be positioned in the passage of the detachable member. A removable handle may be attached to the shaft of the fastener driver. The detachable member, collar, and bone fastener may be substantially co-axial when the fastener driver is positioned in the detachable member. In some embodiments, the removable handle may be attached to the shaft of the fastener driver after the bone fastener, collar, detachable member, and fastener driver combination is positioned down guide wire 218 through a dilator and against a pedicle.

FIGS. 47A-47D depict portions of a procedure for inserting a bone fastener assembly into a patient. Driver 292 (coupled to the bone fastener), and sleeve 244 (coupled to the collar of the bone fastener assembly) may be inserted along guide wire 218 into dilator 302. For spine stabilization procedures using four successively sized dilators, dilator 302 may be fourth dilator 302D. Guide wire 218 represents the trajectory that a bone fastener or bone fastener assembly may follow toward pedicle 164 during insertion of a spine stabilization system. In some embodiments, tissue surrounding the incision may be pulled and/or stretched to allow a desired angular orientation of the bone fastener assembly relative to pedicle 164. FIG. 47A depicts driver 292 and sleeve 244 positioned in dilator 302. After insertion of the bone fastener assembly, sleeve 244, and driver 292 in dilator 302, the driver may be rotated to thread the bone fastener into pedicle 164 and vertebral body 166. The bone fastener may be advanced into the pedicle under fluoroscopic guidance to inhibit breaching of the pedicle walls. When the tip of the bone fastener advances beyond the posterior margin of vertebral body 166, guide wire 218 may be removed to inhibit inadvertent bending of guide wire 218 or unwanted advancement of guide wire 218.

The bone fastener may be advanced to bring the collar down snug to the facet joint. The bone fastener may then be backed off about a quarter of a turn. Backing the fastener off about a quarter of a turn may allow for full motion of the collar relative to the bone fastener. FIG. 47B depicts driver 292 after the bone fastener has been advanced to the desired depth. After the bone fastener has been advanced to the desired depth, driver 292 may be removed from the head of the bone fastener and from dilator 302. FIG. 47C depicts dilator 302 and sleeve 244 after removal of the driver. After removal of the driver, dilator 302 may be removed from the patient. FIG. 47D depicts collar 112 of bone fastener assembly and sleeve 244 after removal of the dilator.

After the bone fastener has been secured to the vertebra and the driver has been removed from the sleeve, the polyaxial nature of the collar may allow angulation of the sleeve relative to the bone fastener. Tissue surrounding the incision may be released such that the sleeve is angled toward a central location between vertebrae to be stabilized. The sleeve may be moved to facilitate positioning of instruments and/or to facilitate access to the adjacent vertebra that is to be stabilized. For example, the sleeve may be tilted towards the adjacent pedicle so that additional length of an opening in the patient is not needed. The channel in the sleeve may be turned toward the adjacent pedicle that is to be stabilized with the spine stabilization system being formed.

A rod may be cut to length and contoured as desired. For example, a medical practitioner may use experience and judgment to determine curvature of a rod for a patient. A desired curvature for the rod may be determined using fluoroscopic imaging. In some embodiments, a curvature of the rod may be chosen such that, when the rod is secured to the collars of the bone fastener assemblies, sleeves coupled to the bone fastener assemblies cross at a surface of the skin. Crossing of the sleeves at a surface of the skin allows the medical practitioner to minimize trauma to a patient by minimizing incision length and tissue plane area. The rod may be bent or shaped with a tool (e.g., a rod bender) to allow insertion of the rod through channels of sleeves with various spatial locations and/or various angular orientations.

Figure 48:
FIG. 48 depicts a side view of one embodiment of a rod.
Figure 49:
FIG. 49 depicts a side view of one embodiment of a rod.
Figure 50:
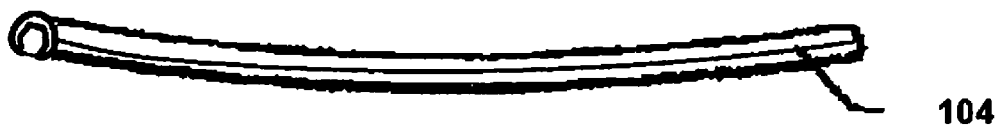
FIG. 50 depicts a side view of one embodiment of a rod.
Figure 51:
FIG. 51 depicts a side view of one embodiment of a rod.

Rods may have shapes including, but not limited to, straight, bent, curved, s-shaped, and z-shaped. FIG. 48 depicts one embodiment of S-shaped rod 104. FIG. 49 depicts one embodiment of rod 104 in which the curvature of rod 104 may be configured with any radius within a range of radii. In some embodiments, the curvature of rod 104 may have multiple curves of different radii (for example, multiple level stabilizations). FIG. 50 depicts one embodiment of bent rod 104. FIG. 51 depicts one embodiment of straight rod 104. In some embodiments, rods 104 may have a substantially circular longitudinal cross section. In certain embodiments, rods 104 may have other cross-sectional shapes including, but not limited to, regular shapes (oval, rectangular, rhomboidal, square) and irregular shapes. An instrumentation kit for a spine stabilization system may include straight rods and/or pre-shaped rods. Straight rods and/or pre-shaped rods may be contoured to accommodate patient anatomy if needed during the surgical procedure.

With the rod satisfactorily positioned, the rod may be secured in place with closure members. To ensure alignment of thread of closure member with thread of collar, the driver may initially be rotated in a direction that would result in removal of the closure member from the collar. When the user of the driver feels engagement of threading of the closure member with threading of the collar, the user may reverse the direction of rotation of the driver to secure the closure member to the driver. The closure member may secure the rod to the collar. Sleeve 244A may serve as a coaxial guide to inhibit cross-threading during insertion of closure members 106. When the closure members are snug and rod 104 is secured, collars 112 are angled such that slots in the collars are substantially perpendicular to the rod. Driver 354 may be disengaged from the closure member and removed from sleeve 244.

In some embodiments, counter torque wrench 368 shown in FIG. 42 may be used to inhibit application of torque to a patient's spine. Counter torque wrench sleeve 370 may be inserted through the opening in the body over sleeve 244. Counter torque wrench sleeve 370 may be advanced toward the spine until rod 104 is seated in groove 374 of the counter torque wrench sleeve. Force may be applied to counter torque wrench 368 in a direction opposite to rotational force applied to a driver used to secure a closure member.

After a closure member is successfully secured to a collar, the driver may be removed from the sleeve coupled to the anchored bone fastener assembly. FIG. 52A depicts an assembled spine stabilization system following removal of driver 354 and wire 400. Key 262, shown in FIG. 52B, may be used to rotate movable members in sleeves 244A, 244B. Rotation of movable members in sleeves 244A, 244B may release the movable members from the collars. Thus, sleeves 244A, 244B may be uncoupled from the collars above the incision. FIG. 52C depicts assembled spine stabilization system 100 following removal of sleeve 244A. FIG. 52D depicts assembled spine stabilization system 100 coupled to adjacent pedicles following removal of sleeve 244B.

A spine stabilization system may be used to stabilize two or more vertebral levels (i.e., at least three adjacent vertebrae). In one embodiment, an incision may be made in the skin between the outermost vertebrae to be stabilized. A first bone fastener assembly may be coupled to a first sleeve. The first bone fastener may be threaded into a first pedicle at a target location such that the first sleeve extends above the body surface. The first sleeve may rotate about the head of the first bone fastener. A second bone fastener assembly may be coupled to a second sleeve and threaded into the second pedicle through a second incision. A third bone fastener assembly may be coupled to a third sleeve and threaded into the third pedicle through a third incision.

In one embodiment of a method for a two-level spine stabilization procedure, three incisions may be made above three target locations over three pedicles. A first bone fastener may be anchored to the middle pedicle. After the first bone fastener is secured, second and third bone fasteners may be coupled to outer pedicles as desired by advancing the second and third bone fastener assemblies via second and third incisions to outer pedicles. A wire may be inserted into the patient via a fourth incision and advanced through the bone fastener assemblies. A rod or two or more segments forming a rod may be advanced via the fourth incision and passed through the collars. After a rod has been positioned and seated in collars as desired, closure members may be used to secure the rod to the collars. One or more counter torque wrenches may be used during shearing of the tool portions of the closure members. In one embodiment, counter torque wrench 364, depicted in FIG. 42, may be used with sleeves 244. Counter torque wrench 368, depicted in FIG. 43, may be used with multi-channel sleeves and/or single-channel sleeves.

Further modifications and alternative embodiments will be apparent to those skilled in the art in view of this description. Accordingly, this description is to be construed as illustrative only and is for the purpose of teaching those skilled in the art the general manner of carrying out the teachings of the disclosure. It is to be understood that the embodiments shown and described herein are to be taken as the presently preferred embodiments. Elements and materials may be substituted for those illustrated and described herein, parts and processes may be reversed, and certain features may be utilized independently, all as would be apparent to one skilled in the art after having the benefit of this disclosure. Changes may be made in the elements described herein without departing from the spirit and scope of the following claims.

What is claimed is:

1. A system for stabilizing a portion of a spine, comprising:
   a rod having:
      a non-circular cross-sectional profile
      a curvature along a length of the rod; and
      a recessed portion located along the length and oriented transverse to a longitudinal axis of the rod;
   two bone fastener assemblies, wherein each bone fastener assembly comprises:
      a pedicle screw for advancement into a vertebra;
      a collar for coupling the rod to the pedicle screw, comprising:
         two upwardly extending walls forming a passage having a profile for receiving a portion of the rod non-circular cross-sectional profile; and
         a threaded portion; and
      a threaded closure member for engaging the threaded portion of the collar to couple the rod in the passage; and
   a wire for percutaneous advancement of the rod to the passage in a bone fastener assembly coupled to a vertebra, wherein the wire comprises:
      a non-circular cross-sectional profile complementary to the rod non-circular cross-sectional profile for engaging the rod to inhibit rotational movement of the rod relative to the wire; and
      a cross-sectional profile and a curvature for engaging the recessed portion of the rod.

2. The system of claim 1, wherein the rod non-circular cross-sectional profile comprises an array of surfaces.

3. The system of claim 1, wherein the rod non-circular cross-sectional profile comprises a flange.

4. The system of claim 1, wherein the rod non-circular cross-sectional profile comprises a slot.

5. The system of claim 1, wherein the rod comprises a cannulated passage along a length thereof.

6. The system of claim 1, wherein the rod comprises:
   two segments, wherein each segment comprises:
      a complementary non-circular cross-sectional profile for engaging the non-circular cross-sectional profile of the wire to inhibit rotational movement of the segment relative to the wire;
      a surface for engagement with a collar;
      a leading end for displacing tissue during advancement of a segment along the wire; and
      a trailing end comprising an engagement feature for connecting with an adjacent segment,
   wherein connecting the two segments forms a rod,
   wherein connecting the two segments of the rod to the two bone fastener assemblies spans a vertebral level.

7. The system of claim 6, wherein each segment comprises a passage through a portion thereof.

8. The system of claim 7, wherein the passage extends along a central axis.

9. The system of claim 7, wherein the passage is offset from a central axis.

10. The system of claim 7, wherein the passage is oriented askew to a longitudinal axis.

11. The system of claim 1, wherein the recessed portion of the rod comprises a passage through a portion of the rod and oriented at a selected angle relative to the longitudinal axis.

12. The system of claim 1, wherein the recessed portion of the rod comprises a groove extending around at least a portion of the outer surface.

13. The system of claim 1, wherein the passage comprises a first passage for receiving a portion of the wire and second passage for receiving a portion of the rod, wherein engaging the closure member in the collar when a wire is positioned in the first passage and when a rod is positioned in the second passage couples the bone screw to the wire and the rod.

14. The system of claim 1, wherein the passage comprises a first passage for receiving a portion of the wire and second passage for receiving a portion of the rod, wherein engaging the closure member in the collar when a wire is positioned in the first passage and when a rod is positioned in the second passage couples the bone screw to the rod and provides clearance for withdrawal of the wire from the bone screw.

15. A method for stabilizing a portion of a spine, comprising the steps of:
   making a first incision for anchoring a first bone fastener assembly in a first vertebra, wherein a bone fastener assembly comprises:
      a bone screw comprising:
         a threaded shank for engaging a portion of a vertebra; and
         a head portion connected to the threaded shank; and
      a collar comprising:
         a bottom portion having an opening for receiving a portion of a bone screw; and
         two upwardly extending walls forming a first passage for receiving the rod and forming a second passage for receiving a portion of a wire;
         a threaded portion; and
      a threaded closure member threaded for engaging the threaded portion of the collar;

making a second incision for anchoring a second bone fastener assembly in a second vertebra;
making a third incision for entry of a wire comprising a non-circular cross sectional profile;
making a fourth incision for exiting of the wire;
advancing the wire through the third incision for positioning near the first and second bone fastener assemblies;
engaging a rod with the wire, wherein the rod comprises:
   a non-circular cross-sectional profile, wherein the rod non-circular cross-sectional profile is complementary to the wire non-circular cross-sectional profile for engaging the wire to inhibit rotational movement of the rod relative to the wire;
rotating the wire to rotate the rod; and
securing the rod to the first and second bone screws, wherein the rod spans at least one vertebral level.

16. The method of claim 15, wherein the rod comprises two or more segments, wherein the method comprises:
engaging a first segment of a rod to the wire, wherein each segment comprises:
   a complementary non-circular cross-sectional profile for engaging the non-circular cross-sectional profile of the wire to inhibit rotational movement of the segment relative to the wire;
   a surface for engagement with a collar;
   a leading end for displacing tissue during advancement of a segment along the wire; and
   a trailing end comprising an engagement feature for connecting with the leading end of an adjacent segment,
wherein connection of one or more segments of the rod to two or more collars spans one or more vertebral levels;
advancing the first segment along the wire to a second passage in the first collar;
engaging a second segment of the rod to the wire;
advancing the second segment to a second passage in the second collar; and
connecting the leading end of the second segment with the trailing end of the first segment to span a vertebral level with a rod having first and second curvatures.

17. A method for advancing a rod into a body, comprising:
advancing a first bone fastener assembly via a first incision in the body, wherein a bone fastener assembly comprises:
a bone screw having a threaded portion and a head portion; and
a collar comprising a opening for receiving the head portion of the bone screw and an opening oriented transverse to the opening for receiving the head portion;
anchoring the first bone fastener assembly to a first vertebra;
advancing a second bone fastener assembly via a second incision in the body;
anchoring the second bone fastener assembly to a second vertebra;
advancing a wire into the body via a third incision, wherein the wire comprises a non-circular cross-sectional profile;
advancing the wire through the transverse openings in the first and second bone fastener assemblies to define a path;
advancing the wire out of the body via a fourth incision;
engaging a rod with the wire, wherein a rod comprises a non-circular cross-sectional profile complementary to the wire cross-sectional profile; and
advancing the rod through the transverse openings in the first and second bone fastener assemblies along the path,
wherein a rod comprises a non-circular cross-sectional profile complementary to the wire cross-sectional profile,
wherein the wire maintains radial orientation of the rod during advancement along the wire.

18. The method of claim 17, wherein the rod comprises a passage along a portion thereof, wherein the step of advancing the rod comprises moving the rod along the wire.

19. The method of claim 17, wherein the rod comprises an attachment feature for attaching the rod to the wire, wherein the step of advancing the rod comprises moving the wire.

20. The method of claim 17, wherein the step of advancing the rod comprises advancing the rod from the third incision to the fourth incision.

21. The method of claim 17, wherein the step of advancing the rod comprises advancing the rod from the fourth incision to the third incision.

22. The method of claim 17, wherein the rod comprises two segments, wherein each segment comprises:
a surface for engagement with a collar;
a leading end for displacing tissue during advancement through the body; and
a trailing end comprising a connection feature for connecting with an adjacent segment, wherein connecting the two segments forms a rod,
wherein engaging the two connected segments to the two bone fastener assemblies spans a vertebral level.

* * * * *